United States Patent
Ogino et al.

(10) Patent No.: US 10,214,508 B2
(45) Date of Patent: Feb. 26, 2019

(54) NITROGEN-CONTAINING HETEROCYCLIC COMPOUND

(71) Applicant: Takeda Pharmaceutical Company Limited, Osaka-shi, Osaka (JP)

(72) Inventors: Masaki Ogino, Kanagawa (JP); Eiji Kimura, Kanagawa (JP); Shinkichi Suzuki, Kanagawa (JP); Tomoko Ashizawa, Kanagawa (JP); Toshihiro Imaeda, New York, NY (US); Ikuo Fujimori, Kanagawa (JP); Ryosuke Arai, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/318,552

(22) PCT Filed: Jun. 11, 2015

(86) PCT No.: PCT/JP2015/066907
§ 371 (c)(1),
(2) Date: Dec. 13, 2016

(87) PCT Pub. No.: WO2015/190564
PCT Pub. Date: Dec. 17, 2015

(65) Prior Publication Data
US 2017/0121308 A1 May 4, 2017

(30) Foreign Application Priority Data
Jun. 13, 2014 (JP) ................................ 2014-122919

(51) Int. Cl.
| | | |
|---|---|---|
| *C07D 401/10* | (2006.01) |
| *C07D 401/14* | (2006.01) |
| *C07D 405/14* | (2006.01) |
| *A61K 31/44* | (2006.01) |
| *A61K 31/4439* | (2006.01) |
| *A61K 31/444* | (2006.01) |
| *C07D 213/81* | (2006.01) |
| *C07D 405/12* | (2006.01) |

(52) U.S. Cl.
CPC ............ *C07D 401/10* (2013.01); *A61K 31/44* (2013.01); *A61K 31/444* (2013.01); *A61K 31/4439* (2013.01); *C07D 213/81* (2013.01); *C07D 401/14* (2013.01); *C07D 405/12* (2013.01); *C07D 405/14* (2013.01)

(58) Field of Classification Search
CPC .................................................. C07D 401/10
USPC ...................... 546/275.4; 514/341
See application file for complete search history.

(56) References Cited

U.S. PATENT DOCUMENTS

| | | |
|---|---|---|
| 2008/0269234 A1 | 10/2008 | Gandhi et al. |
| 2011/0301122 A1 | 12/2011 | Harter et al. |
| 2012/0252808 A1 | 10/2012 | Kuduk et al. |
| 2013/0217692 A1 | 8/2013 | Horiuchi et al. |
| 2015/0126487 A1 | 5/2015 | Sakamoto et al. |
| 2015/0307497 A1 | 10/2015 | Sugimoto et al. |
| 2016/0016907 A1 | 1/2016 | Brodney et al. |
| 2017/0081332 A1 | 3/2017 | Sugimoto |

FOREIGN PATENT DOCUMENTS

| | | |
|---|---|---|
| WO | 2007/138110 | 12/2007 |
| WO | 2010/025179 | 3/2010 |
| WO | 2010/054764 | 5/2010 |
| WO | 2011117254 | 9/2011 |
| WO | 2011/159554 | 12/2011 |
| WO | 2012/003544 | 1/2012 |
| WO | 2012/118563 | 9/2012 |
| WO | 2013/129622 | 9/2013 |
| WO | 2014077401 | 5/2014 |
| WO | 2014/086705 | 6/2014 |
| WO | 2015/163485 | 10/2015 |
| WO | 2015/174534 | 11/2015 |
| WO | 2016/009297 | 1/2016 |

OTHER PUBLICATIONS

Layzer et al., "Section Five-Degenerative Diseases of the Nervous System", Cecil Textbook of Medicine, 20th edition, vol. 2, pp. 2050-2057 (Year: 1996).*

(Continued)

*Primary Examiner* — Patricia L Morris
(74) *Attorney, Agent, or Firm* — Hamre, Schumann, Mueller & Larson, P.C.

(57) ABSTRACT

The present invention provides a compound having a cholinergic muscarinic M1 receptor positive allosteric modulator activity and useful as a medicament such as a prophylactic or therapeutic drug for Alzheimer's disease, schizophrenia, pain, sleep disorder, Parkinson's disease dementia, dementia with Lewy bodies and the like, and the like. The present invention relates to a compound represented by the formula (I) or a salt thereof.

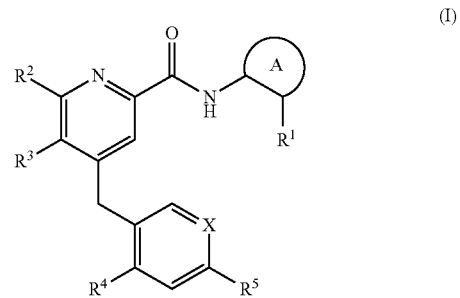

wherein each symbol is as described in the attached DESCRIPTION.

6 Claims, No Drawings

(56) References Cited

OTHER PUBLICATIONS

Carruthers et al., "The muscarinic system, etc.," Neuroscience and Biobehavioral Reviews 55 ,393-402. (Year: 2015).*
Verma et al., "Muscarinic and, etc.," Journal of Pharmacy and Pharmacology, 70, 985-993. (Year: 2018).*
Martino et al., The M1/M4 preferring, etc., Pain 152, 2852-2860. (Year: 2011).*
Scarr et al., "Muscarinic receptors, etc.," Journal of Neurochemistry, 107, 1188-1195. (Year: 2008).*
Wess, et al., "Mascarinic acetylcholine receptors: mutant mice provide new insights for drug development", Nature Reviews Drug Discovery, vol. 6, Sep. 2007, pp. 721-733.
Davoren, et al. "Discovery of the Potent and Selective M1 PAM-Agonist N-[(3R,4S)-3-Hydroxytetrahydro-2H-pyran-4-yl]-5-methyl-4-[4-(1,3-thiazol-4-yl)benzyl]pyridine-2-carboxamide (PF-06767832): Evaluation of Efficacy and Cholinergic Side Effects", Journal of Medicinal Chemistry, vol. 59, 2016, pp. 6313-6328.
International Search Report issued in International Application No. PCT/JP2015/066907, dated Sep. 1, 2015, 4 pages.

\* cited by examiner

NITROGEN-CONTAINING HETEROCYCLIC COMPOUND

TECHNICAL FIELD

The present invention relates to a nitrogen-containing heterocyclic compound having a cholinergic muscarinic M1 receptor positive allosteric modulator activity and useful as a medicament such as a prophylactic or therapeutic drug for Alzheimer's disease, schizophrenia, pain, sleep disorder, Parkinson's disease dementia, dementia with Lewy bodies and the like, and the like. As used herein, the positive allosteric modulator activity refers to an action to potentiate receptor function by binding to a moiety different from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the central nervous system, nuclei of origin of the acetylcholine neuron are in the brain stem and forebrain, and those acetylcholine neurons project to cerebral cortex, hippocampus, and limbic area. In addition, some interneurons in some brain areas such as striatum utilize acetylcholine as a neurotransmitter. Acetylcholine receptor is classified into a ligand dependent ion channel (cholinergic nicotinic receptor) and a G-protein-conjugated receptor (cholinergic muscarinic receptor). The cholinergic muscarinic receptor is one kind of receptor for excitatory neurotransmitter acetylcholine, and was named based on the selective activation of the receptor by muscarine. The muscarinic receptor is further classified into subtypes of M1 to M5, and the M1 receptor is known to be widely distributed mainly in the brain, and deeply involved particularly in learning, memory, sleep, neuropathic pain and the like. The importance of cholinergic muscarinic M1 receptor in brain physiology is well known, and a compound having an M1 receptor function enhancing action is expected to be useful as a prophylactic or therapeutic drug for mental diseases, neurodegenerative diseases, memory disorders, pain, sleep disorders and the like (non-patent document 1).

WO 2011/117254 A1 (patent document 1) discloses the following compound as a modulator of ghrelin receptor.

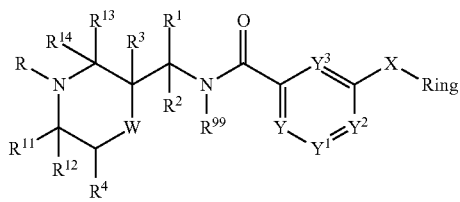

wherein each symbol is as defined in the document.

US 2008/0269234 A1 (patent document 2) discloses the following compound as a poly(ADP-ribose)polymerase inhibitor.

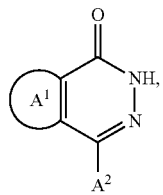

wherein each symbol is as defined in the document.

WO 2010/025179 A1 (patent document 3) discloses the following compound as a liver X receptor (LXRα and LxRβ) modulator.

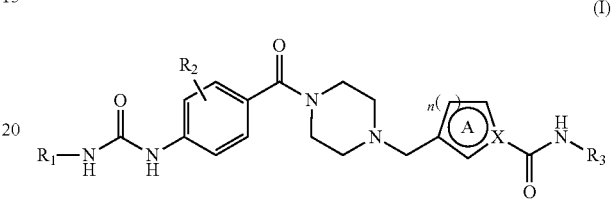

wherein each symbol is as defined in the document.

WO 2012/003544 A1 (patent document 4) discloses the following compound as a protein kinase inhibitor.

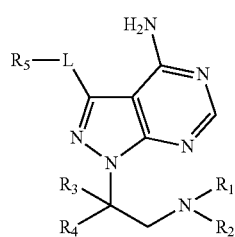

wherein each symbol is as defined in the document.

WO 2010/054764 A1 (patent document 5) discloses the following compound as a HIF inhibitor.

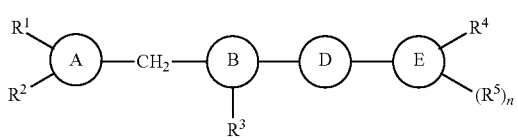

wherein each symbol is as defined in the document.

WO 2013/129622 A1 (patent document 6) discloses the following compound as a compound having an M1PAM activity, and effective for Alzheimer's disease and the like.

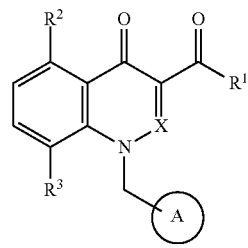

wherein each symbol is as defined in the document.

WO 2014/077401 A1 (patent document 7) discloses the following compound having a cholinergic muscarinic M1 receptor positive allosteric modulator activity and useful as a prophylactic or therapeutic drug for Alzheimer's disease, schizophrenia, pain, sleep disorder and the like.

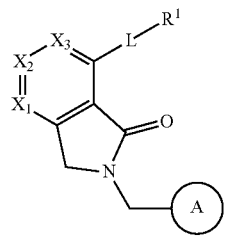
(I)

wherein each symbol is as defined in the document.

DOCUMENT LIST

Patent Documents patent document 1: WO 2011/117254 A1
patent document 2: US 2008/0269234 A1
patent document 3: WO 2010/025179 A1
patent document 4: WO 2012/003544 A1
patent document 5: WO 2010/054764 A1
patent document 6: WO 2013/129622 A1
patent document 7: WO 2014/077401 A1

Non-Patent Document non-patent document 1: Nature Reviews Drug Discovery, 2007, 6, 721-733.

SUMMARY OF THE INVENTION

Problems to be Solved by the Invention

The development of a compound having a cholinergic muscarinic M1 receptor (M1 receptor) positive allosteric modulator activity and useful as a prophylactic or therapeutic drug for Alzheimer's disease, schizophrenia, pain, sleep disorder, Parkinson's disease dementia, dementia with Lewy bodies and the like is desired. As used herein, the positive allosteric modulator activity means an action to bind to a site different from an endogenous activator (acetylcholine in this receptor) and potentiate the receptor function.

Means of Solving the Problems

The present inventors have conducted intensive studies in an attempt to solve the aforementioned problems and found that a compound represented by the following formula (I) has a cholinergic muscarinic M1 receptor positive allosteric modulator activity, which resulted in the completion of the present invention.

Therefore, the present invention relates to the following.
[1] A compound represented by the formula (I):

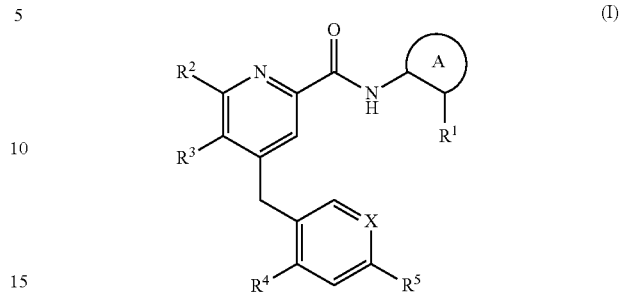
(I)

wherein
A is a cyclic group which is optionally further substituted;
$R^1$ is a hydrogen atom or a hydroxyl group;
$R^2$ and $R^3$ are each independently a hydrogen atom, a halogen atom, a cyano group, an optionally substituted $C_{1-6}$ alkyl group, an optionally substituted $C_{2-6}$ alkenyl group, an optionally substituted $C_{3-6}$ cycloalkyl group, or an optionally substituted $C_{1-6}$ alkoxy group;
$R^4$ is a hydrogen atom or a halogen atom;
$R^5$ is an optionally substituted 5- or 6-membered aromatic heterocyclic group, a halogen atom, a cyano group, an optionally substituted $C_{1-6}$ alkyl group, or an optionally substituted $C_{1-6}$ alkoxy group; and
X is CH or N,
or a salt thereof (hereinafter sometimes to be referred to as compound (I));
[2] a compound represented by the formula (I):

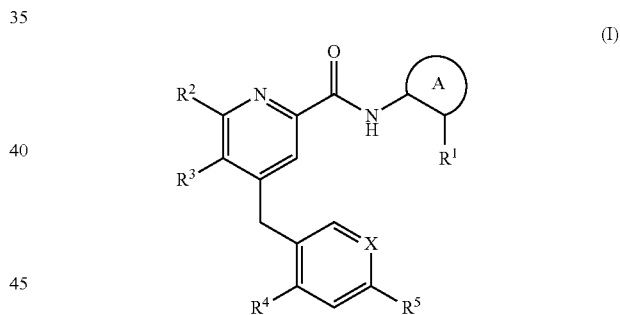
(I)

wherein
A is a cyclic group which is optionally further substituted;
$R^1$ is a hydrogen atom or a hydroxyl group;
$R^2$ and $R^3$ are each independently a hydrogen atom, a halogen atom, a cyano group, an optionally substituted $C_{1-6}$ alkyl group, an optionally substituted $C_{2-6}$ alkenyl group, an optionally substituted $C_{3-6}$ cycloalkyl group, or an optionally substituted $C_{1-6}$ alkoxy group;
$R^4$ is a hydrogen atom or a halogen atom;
$R^5$ is optionally substituted pyrazolyl group, a halogen atom, a cyano group, an optionally substituted $C_{1-6}$ alkyl group, or an optionally substituted $C_{1-6}$ alkoxy group; and
X is CH or N,
or a salt thereof (hereinafter sometimes to be referred to as compound (I));
[3] the compound of [1] or [2], wherein at least one of $R^2$ and $R^3$ is a substituent, or a salt thereof;
[4] the compound of [1], wherein A is
(i) a $C_{3-10}$ cycloalkyl group optionally fused with a benzene ring, or (ii) a nonaromatic heterocyclic group, each of which is optionally further substituted by 1 to 3 substituents selected from
(1) a halogen atom,
(2) an optionally substituted $C_{1-6}$ alkyl group, and
(3) an optionally substituted $C_{1-6}$ alkoxy group;
$R^1$ is a hydrogen atom or a hydroxyl group;
$R^2$ is a hydrogen atom, an optionally substituted $C_{1-6}$ alkyl group or optionally substituted $C_{1-6}$ alkoxy group;
$R^3$ is a hydrogen atom, a halogen atom, a cyano group, an optionally substituted $C_{1-6}$ alkyl group, an optionally substituted $C_{2-6}$ alkenyl group, an optionally substituted $C_{3-6}$ cycloalkyl group, or an optionally substituted $C_{1-6}$ alkoxy group;
$R^4$ is a hydrogen atom or a halogen atom;
$R^5$ is an optionally substituted 5- or 6-membered aromatic heterocyclic group, a halogen atom, a cyano group, a $C_{1-6}$ alkyl group, or a $C_{1-6}$ alkoxy group; and
X is CH or N,
or a salt thereof;
[5] the compound of [1] or [2], wherein A is
(i) a $C_{3-10}$ cycloalkyl group optionally fused with a benzene ring,
(ii) an oxetanyl group,
(iii) a tetrahydrofuranyl group, or
(iv) a tetrahydropyranyl group, each of which is optionally further substituted by 1 to 3 substituents selected from
(1) a halogen atom,
(2) a $C_{1-6}$ alkyl group optionally substituted by 1 to 3 hydroxy groups, and
(3) a $C_{1-6}$ alkoxy group;
$R^1$ is a hydrogen atom or a hydroxyl group;
$R^2$ is a hydrogen atom, a $C_{1-6}$ alkyl group or a $C_{1-6}$ alkoxy group;
$R^3$ is a hydrogen atom, a halogen atom, a cyano group, a $C_{1-6}$ alkyl group optionally substituted by 1 to 3 halogen atoms, a $C_{2-6}$ alkenyl group, a $C_{3-6}$ cycloalkyl group, or a $C_{1-6}$ alkoxy group optionally substituted by 1 to 3 halogen atoms;
$R^4$ is a hydrogen atom or a halogen atom;
$R^5$ is a pyrazolyl group optionally substituted by 1 to 3 $C_{1-6}$ alkyl groups, a halogen atom, a cyano group, a $C_{1-6}$ alkyl group, or a $C_{1-6}$ alkoxy group; and
X is CH or N,
or a salt thereof;
[6] the compound of [1] or [2], wherein A is
(i) a $C_{3-10}$ cycloalkyl group, or
(ii) a tetrahydropyranyl group;
$R^1$ is a hydroxyl group;
$R^2$ is a hydrogen atom or a $C_{1-6}$ alkyl group;
$R^3$ is a halogen atom, a cyano group, a $C_{1-6}$ alkyl group, or a $C_{1-6}$ alkoxy group;
$R^4$ is a hydrogen atom;
$R^5$ is a pyrazolyl group optionally substituted by 1 to 3 $C_{1-6}$ alkyl groups or a halogen atom; and
X is CH or N,
or a salt thereof;
[7] the compound of [1] or [2], wherein A is a $C_{3-10}$ cycloalkyl group;
$R^1$ is a hydroxyl group;
$R^2$ is a hydrogen atom or a $C_{1-6}$ alkyl group;
$R^3$ is a $C_{1-6}$ alkyl group;
$R^4$ is a hydrogen atom;
$R^5$ is a pyrazolyl group optionally substituted by 1 to 3 $C_{1-6}$ alkyl groups; and
X is CH or N,
or a salt thereof;

[8] N-((1S,2S)-2-hydroxycyclopentyl)-5-methyl-4-(4-(1-methyl-1H-pyrazol-3-yl)benzyl)pyridine-2-carboxamide or a salt thereof;
[9] N-((1S,2S)-2-hydroxycyclopentyl)-5,6-dimethyl-4-(4-(1-methyl-1H-pyrazol-3-yl)benzyl)pyridine-2-carboxamide or a salt thereof;
[10] N-((1S,2S)-2-hydroxycyclohexyl)-5,6-dimethyl-4-((6-(1-methyl-1H-pyrazol-3-yl)pyridin-3-yl)methyl)pyridine-2-carboxamide or a salt thereof;
[11] a medicament comprising the compound of the above-mentioned [1] or [2] or a salt thereof;
[12] the medicament of the above-mentioned [11], which is a cholinergic muscarinic M1 receptor positive allosteric modulator;
[13] the medicament of the above-mentioned [11], which is a prophylactic or therapeutic agent for Alzheimer's disease, schizophrenia, pain, a sleep disorder, Parkinson's disease dementia, or dementia with Lewy bodies;
[14] the compound of the above-mentioned [1] or [2] or a salt thereof for use in the prophylaxis or treatment of Alzheimer's disease, schizophrenia, pain, a sleep disorder, Parkinson's disease dementia, or dementia with Lewy bodies;
[15] a method of cholinergic muscarinic M1 receptor positive allosteric modulation in a mammal, comprising administering an effective amount of the compound of the aforementioned [1] or [2] or a salt thereof to said mammal;
[16] a method for the prophylaxis or treatment of Alzheimer's disease, schizophrenia, pain, a sleep disorder, Parkinson's disease dementia, or dementia with Lewy bodies in a mammal, comprising administering an effective amount of the compound of the aforementioned [1] or [2] or a salt thereof to said mammal;
[17] use of the compound of the aforementioned [1] or [2] or a salt thereof in the production of a prophylactic or therapeutic agent for Alzheimer's disease, schizophrenia, pain, a sleep disorder, Parkinson's disease dementia, or dementia with Lewy bodies.

Effect of the Invention

The compound of the present invention has a cholinergic muscarinic M1 receptor positive allosteric modulator activity, and is useful as a medicament such as a prophylactic or therapeutic drug for, for example, Alzheimer's disease, schizophrenia, pain, sleep disorder, Parkinson's disease dementia, dementia with Lewy bodies and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkyl-sulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ aryl-sulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthyl carbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic m group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include the "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methyl-amino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocylyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "cyclic group" of the "optionally substituted cyclic group" include the above-mentioned "$C_{3-10}$ cycloalkyl group", "$C_{3-10}$ cycloalkenyl group", "$C_{6-14}$ aryl group" and "heterocyclic group", and examples of the substituent thereof include the above-mentioned "substituent".

In the present specification, examples of the "5- or 6-membered aromatic heterocyclic group" of the "optionally substituted 5- or 6-membered aromatic heterocyclic group" include 5- or 6-membered ones from the above-mentioned "aromatic heterocyclic group", and examples of the substituent thereof include the above-mentioned "substituent".

In the present specification, examples of the "5- or 6-membered nitrogen-containing aromatic heterocyclic group" of the "optionally substituted 5- or 6-membered nitrogen-containing aromatic heterocyclic group" include 5- or 6-membered ones from the above-mentioned "aromatic heterocyclic group" and containing at least one nitrogen atom as a ring-constituting atom, and examples of the substituent thereof include the above-mentioned "substituent".

In the present specification, examples of the "$C_{3-6}$ cycloalkyl group" include the above-mentioned "$C_{3-10}$ cycloalkyl group" having a carbon number of 3-6.

The definition of each symbol in the formula (I) is described in detail in the following.

A is a cyclic group which is optionally further substituted.

Examples of the "cyclic group" of the "cyclic group which is optionally further substituted" for A include a $C_{3-10}$ cycloalkyl group (e.g., cyclopropyl, cyclobutyl, cyclopentyl, cyclohexyl) optionally fused with a benzene ring and a nonaromatic heterocyclic group (e.g., oxetanyl, tetrahydrofuranyl, tetrahydropyranyl).

The "cyclic group" of the "cyclic group which is optionally further substituted" for A is optionally further substituted by 1-3 (preferably 1 or 2) substituents at substitutable position(s).

Examples of such "substituent" include a halogen atom (e.g., fluorine atom), an optionally substituted $C_{1-6}$ alkyl group (e.g., methyl), and an optionally substituted $C_{1-6}$ alkoxy group (e.g., methoxy).

A is preferably (i) a $C_{3-10}$ cycloalkyl group (e.g., cyclopropyl, cyclobutyl, cyclopentyl, cyclohexyl) optionally fused with a benzene ring or (ii) a nonaromatic heterocyclic group (e.g., oxetanyl, tetrahydrofuranyl, tetrahydropyranyl), each of which is optionally further substituted by 1-3 (preferably 1 or 2) substituents selected from (1) a halogen atom (e.g., fluorine atom), (2) an optionally substituted $C_{1-6}$ alkyl group (e.g., methyl) and (3) an optionally substituted $C_{1-6}$ alkoxy group (e.g., methoxy), more preferably, (i) a $C_{3-10}$ cycloalkyl group (e.g., cyclopropyl, cyclobutyl, cyclopentyl, cyclohexyl) optionally fused with a benzene ring or (ii) a nonaromatic heterocyclic group (e.g., oxetanyl, tetrahydrofuranyl, tetrahydropyranyl), each of which is optionally further substituted by 1-3 (preferably 1 or 2) substituents selected from (1) a halogen atom (e.g., fluorine atom), (2) a $C_{1-6}$ alkyl group (e.g., methyl) optionally substituted by 1-3 (preferably 1 or 2) hydroxy groups and (3) a $C_{1-6}$ alkoxy group (e.g., methoxy), further preferably, (i) a $C_{3-10}$ cycloalkyl group (e.g., cyclopropyl, cyclobutyl, cyclopentyl, cyclohexyl) optionally fused with a benzene ring which is optionally further substituted by 1-3 (preferably 1 or 2) substituents selected from (1) a halogen atom (e.g., fluorine atom), (2) a $C_{1-6}$ alkyl group (e.g., methyl) optionally substituted by 1-3 (preferably 1 or 2) hydroxy groups and (3) a $C_{1-6}$ alkoxy group (e.g., methoxy), or (ii) a nonaromatic heterocyclic group (e.g., oxetanyl, tetrahydrofuranyl, tetrahydropyranyl).

$R^1$ is a hydrogen atom or a hydroxyl group.

In another embodiment of the present invention, A is preferably cyclopentyl, cyclohexyl or tetrahydropyranyl, and $R^1$ is a hydroxyl group, more preferably, the steric configuration of A is as described below.

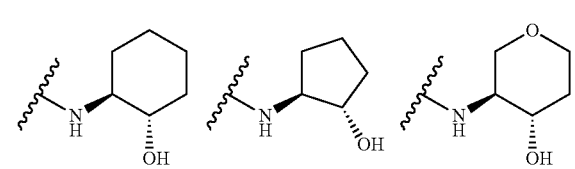

$R^2$ and $R^3$ are each independently a hydrogen atom, a halogen atom, a cyano group, an optionally substituted $C_{1-6}$ alkyl group, an optionally substituted $C_{2-6}$ alkenyl group, an optionally substituted $C_{3-6}$ cycloalkyl group, or an optionally substituted $C_{1-6}$ alkoxy group.

$R^2$ is preferably a hydrogen atom, an optionally substituted $C_{1-6}$ alkyl group (e.g., methyl) or an optionally substituted $C_{1-6}$ alkoxy group (e.g., methoxy), more preferably, a hydrogen atom, a $C_{1-6}$ alkyl group (e.g., methyl) or a $C_{1-6}$ alkoxy group (e.g., methoxy).

$R^3$ is preferably a hydrogen atom, a halogen atom (e.g., fluorine atom, chlorine atom), a cyano group, an optionally substituted $C_{1-6}$ alkyl group (e.g., methyl, ethyl), an optionally substituted $C_{2-6}$ alkenyl group (e.g., vinyl), an optionally substituted $C_{3-6}$ cycloalkyl group (e.g., cyclopropyl), or an optionally substituted $C_{1-6}$ alkoxy group (e.g., methoxy), more preferably, a hydrogen atom, a halogen atom (e.g., fluorine atom, chlorine atom), a cyano group, a $C_{1-6}$ alkyl group (e.g., methyl, ethyl) optionally substituted by 1-3 (preferably 1 or 2) halogen atoms (e.g., fluorine atom), a $C_{2-6}$ alkenyl group (e.g., vinyl), a $C_{3-6}$ cycloalkyl group (e.g., cyclopropyl), or a $C_{1-6}$ alkoxy group (e.g., methoxy) optionally substituted by 1-3 (preferably 1 or 2) halogen atoms (e.g., fluorine atom).

In another embodiment of the present invention, at least one of $R^2$ and $R^3$ is preferably a substituent.

$R^4$ is a hydrogen atom or a halogen atom.

$R^4$ is preferably a hydrogen atom or a fluorine atom.

$R^5$ is an optionally substituted 5- or 6-membered aromatic heterocyclic group, a halogen atom, a cyano group, an optionally substituted $C_{1-6}$ alkyl group, or an optionally substituted $C_{1-6}$ alkoxy group.

$R^5$ is preferably an optionally substituted 5- or 6-membered aromatic heterocyclic group (preferably, 5- or 6-membered nitrogen-containing aromatic heterocyclic group; e.g., pyrazolyl), a halogen atom (e.g., chlorine atom, bromine atom), a cyano group, a $C_{1-6}$ alkyl group (e.g., methyl) or a $C_{1-6}$ alkoxy group (e.g., methoxy), more preferably, a 5- or 6-membered aromatic heterocyclic group (preferably, 5- or 6-membered nitrogen-containing aromatic heterocyclic group; e.g., pyrazolyl) optionally substituted by 1-3 (preferably 1 or 2) $C_{1-6}$ alkyl groups (e.g., methyl, ethyl), a halogen atom (e.g., chlorine atom, bromine atom), a cyano group, a $C_{1-6}$ alkyl group (e.g., methyl) or a $C_{1-6}$ alkoxy group (e.g., methoxy).

In another embodiment of the present invention, $R^5$ is an optionally substituted pyrazolyl group, a halogen atom, a cyano group, an optionally substituted $C_{1-6}$ alkyl group, or an optionally substituted $C_{1-6}$ alkoxy group.

$R^5$ is preferably an optionally substituted pyrazolyl group, a halogen atom (e.g., chlorine atom, bromine atom), a cyano group, a $C_{1-6}$ alkyl group (e.g., methyl) or a $C_{1-6}$ alkoxy group (e.g., methoxy), more preferably, a pyrazolyl group optionally substituted by 1-3 (preferably 1 or 2) $C_{1-5}$ alkyl groups (e.g., methyl, ethyl), a halogen atom (e.g., chlorine atom, bromine atom), a cyano group, a $C_{1-6}$ alkyl group (e.g., methyl) or a $C_{1-6}$ alkoxy group (e.g., methoxy).

In still another embodiment of the present invention, $R^5$ is preferably an optionally substituted pyrazolyl group, more preferably, a pyrazolyl group optionally substituted by 1 or 2 $C_{1-6}$ alkyl groups (e.g., methyl, ethyl).

X is CH or N.

In one embodiment of the present invention, X is preferably CH.

In another embodiment of the present invention, X is preferably N.

Preferable examples of compound (I) include the following compounds.

[Compound I-1]

Compound (I) wherein

A is (i) a $C_{3-10}$ cycloalkyl group (e.g., cyclopropyl, cyclobutyl, cyclopentyl, cyclohexyl) optionally fused with a benzene ring or (ii) a nonaromatic heterocyclic group (e.g., oxetanyl, tetrahydrofuranyl, tetrahydropyranyl), each of which is optionally further substituted by 1-3 (preferably 1 or 2) substituents selected from (1) a halogen atom (e.g., fluorine atom), (2) an optionally substituted $C_{1-6}$ alkyl group (e.g., methyl) and (3) an optionally substituted $C_{1-6}$ alkoxy group (e.g., methoxy);

$R^1$ is a hydrogen atom or a hydroxyl group;

$R^2$ is a hydrogen atom, an optionally substituted $C_{1-6}$ alkyl group (e.g., methyl) or an optionally substituted $C_{1-6}$ alkoxy group (e.g., methoxy);

$R^3$ is a hydrogen atom, a halogen atom (e.g., fluorine atom, chlorine atom), a cyano group, an optionally substituted $C_{1-6}$ alkyl group (e.g., methyl, ethyl), an optionally substituted $C_{2-6}$ alkenyl group (e.g., vinyl), an optionally substituted $C_{3-6}$ cycloalkyl group (e.g., cyclopropyl), or an optionally substituted $C_{1-6}$ alkoxy group (e.g., methoxy);

$R^4$ is a hydrogen atom or a halogen atom (e.g., fluorine atom);

$R^5$ is an optionally substituted 5- or 6-membered aromatic heterocyclic group (preferably, 5- or 6-membered nitrogen-containing aromatic heterocyclic group; e.g., pyrazolyl), a halogen atom (e.g., chlorine atom, bromine atom), a cyano group, a $C_{1-6}$ alkyl group (e.g., methyl) or a $C_{1-6}$ alkoxy group (e.g., methoxy); and X is CH or N.

[Compound I-2]

Compound (I) wherein

A is (i) a $C_{3-10}$ cycloalkyl group (e.g., cyclopropyl, cyclobutyl, cyclopentyl, cyclohexyl) optionally fused with a benzene ring or (ii) a nonaromatic heterocyclic group (e.g., oxetanyl, tetrahydrofuranyl, tetrahydropyranyl), each of which is optionally further substituted by 1-3 (preferably 1 or 2) substituents selected from (1) a halogen atom (e.g., fluorine atom), (2) an optionally substituted $C_{1-6}$ alkyl group (e.g., methyl) and (3) an optionally substituted $C_{1-6}$ alkoxy group (e.g., methoxy);

$R^1$ is a hydrogen atom or a hydroxyl group;

$R^2$ is a hydrogen atom, an optionally substituted $C_{1-6}$ alkyl group (e.g., methyl) or an optionally substituted $C_{1-6}$ alkoxy group (e.g., methoxy);

$R^3$ is a hydrogen atom, a halogen atom (e.g., fluorine atom, chlorine atom), a cyano group, an optionally substituted $C_{1-6}$ alkyl group (e.g., methyl, ethyl), an optionally substituted $C_{2-6}$ alkenyl group (e.g., vinyl), an optionally substituted $C_{3-6}$ cycloalkyl group (e.g., cyclopropyl), or an optionally substituted $C_{1-6}$ alkoxy group (e.g., methoxy);

$R^4$ is a hydrogen atom or a fluorine atom;

$R^5$ is an optionally substituted pyrazolyl group, a halogen atom (e.g., chlorine atom, bromine atom), a cyano group, a $C_{1-6}$ alkyl group (e.g., methyl) or a $C_{1-6}$ alkoxy group (e.g., methoxy); and X is CH or N.

[Compound I-3]

Compound (I) wherein

A is (i) a $C_{3-10}$ cycloalkyl group (e.g., cyclopropyl, cyclobutyl, cyclopentyl, cyclohexyl) optionally fused with a benzene ring, (ii) an oxetanyl group, (iii) a tetrahydrofuranyl group, or (iv) a tetrahydropyranyl group, each of which is optionally further substituted by 1 to 3 substituents selected from (1) a halogen atom (e.g., fluorine atom), (2) an optionally substituted $C_{1-6}$ alkyl group (e.g., methyl), and (3) an optionally substituted $C_{1-6}$ alkoxy group (e.g., methoxy);

$R^1$ is a hydrogen atom or a hydroxyl group;

$R^2$ is a hydrogen atom, an optionally substituted $C_{1-6}$ alkyl group (e.g., methyl) or an optionally substituted $C_{1-6}$ alkoxy group (e.g., methoxy);

$R^3$ is a hydrogen atom, a halogen atom (e.g., fluorine atom, chlorine atom), a cyano group, an optionally substituted $C_{1-6}$ alkyl group (e.g., methyl, ethyl), an optionally substituted $C_{2-6}$ alkenyl group (e.g., vinyl), an optionally substituted $C_{3-6}$ cycloalkyl group (e.g., cyclopropyl), or an optionally substituted $C_{1-6}$ alkoxy group (e.g., methoxy);

$R^4$ is a hydrogen atom or a halogen atom (e.g., fluorine atom);

$R^5$ is an optionally substituted 5- or 6-membered aromatic heterocyclic group (preferably, 5- or 6-membered nitrogen-containing aromatic heterocyclic group; e.g., pyrazolyl), a halogen atom (e.g., chlorine atom, bromine atom), a cyano group, a $C_{1-6}$ alkyl group (e.g., methyl), or a $C_{1-6}$ alkoxy group (e.g., methoxy); and X is CH or N.

[Compound I-4]

Compound (I) wherein

A is (i) a $C_{3-10}$ cycloalkyl group (e.g., cyclopropyl, cyclobutyl, cyclopentyl, cyclohexyl) optionally fused with a benzene ring or (ii) a nonaromatic heterocyclic group (e.g., oxetanyl, tetrahydrofuranyl, tetrahydropyranyl), each of which is optionally further substituted by 1-3 (preferably 1 or 2) substituents selected from (1) a halogen atom (e.g., fluorine atom), (2) a $C_{1-6}$ alkyl group (e.g., methyl) optionally substituted by 1-3 (preferably 1 or 2) hydroxy groups and (3) a $C_{1-6}$ alkoxy group (e.g., methoxy);

$R^1$ is a hydrogen atom or a hydroxyl group;

$R^2$ is a hydrogen atom, a $C_{1-6}$ alkyl group (e.g., methyl) or a $C_{1-6}$ alkoxy group (e.g., methoxy);

$R^3$ is a hydrogen atom, a halogen atom (e.g., fluorine atom, chlorine atom), a cyano group, a $C_{1-6}$ alkyl group (e.g., methyl, ethyl) optionally substituted by 1-3 (preferably 1 or 2) halogen atoms (e.g., fluorine atom), a $C_{2-6}$ alkenyl group (e.g., vinyl), a $C_{3-6}$ cycloalkyl group (e.g., cyclopropyl), or a $C_{1-6}$ alkoxy group (e.g., methoxy) optionally substituted by 1-3 (preferably 1 or 2) halogen atoms (e.g., fluorine atom);

$R^4$ is a hydrogen atom or a fluorine atom;

$R^5$ is a pyrazolyl group optionally substituted by 1-3 (preferably 1 or 2) $C_{1-6}$ alkyl groups (e.g., methyl, ethyl), a halogen atom (e.g., chlorine atom, bromine atom), a cyano group, a $C_{1-6}$ alkyl group (e.g., methyl) or a $C_{1-6}$ alkoxy group (e.g., methoxy); and X is CH or N.

[Compound I-5]

Compound (I) wherein

A is (i) a $C_{3-10}$ cycloalkyl group (e.g., cyclopropyl, cyclobutyl, cyclopentyl, cyclohexyl) optionally fused with a benzene ring, (ii) an oxetanyl group, (iii) a tetrahydrofuranyl group, or (iv) a tetrahydropyranyl group, each of which is optionally further substituted by 1 to 3 substituents selected from (1) a halogen atom (e.g., fluorine atom), (2) a $C_{1-6}$ alkyl group (e.g., methyl) optionally substituted by 1 to 3 hydroxy groups, and (3) a $C_{1-6}$ alkoxy group (e.g., methoxy);

$R^1$ is a hydrogen atom or a hydroxyl group;

$R^2$ is a hydrogen atom, a $C_{1-6}$ alkyl group (e.g., methyl) or a $C_{1-6}$ alkoxy group (e.g., methoxy);

$R^3$ is a hydrogen atom, a halogen atom (e.g., fluorine atom, chlorine atom), a cyano group, a $C_{1-6}$ alkyl group (e.g., methyl, ethyl) optionally substituted by 1 to 3 halogen atoms (e.g., fluorine atom), a $C_{2-6}$ alkenyl group (e.g., vinyl), a $C_{3-6}$ cycloalkyl group (e.g., cyclopropyl), or a $C_{1-6}$ alkoxy group (e.g., methoxy) optionally substituted by 1 to 3 halogen atoms (e.g., fluorine atom);

$R^4$ is a hydrogen atom or a halogen atom (e.g., fluorine atom);

$R^5$ is a pyrazolyl group optionally substituted by 1 to 3 $C_{1-6}$ alkyl groups (e.g., methyl, ethyl), a halogen atom (e.g., chlorine atom, bromine atom), a cyano group, a $C_{1-6}$ alkyl group (e.g., methyl), or a $C_{1-6}$ alkoxy group (e.g., methoxy); and X is CH or N.

[Compound I-6]

Compound (I) wherein

A is (i) a $C_{3-10}$ cycloalkyl group (e.g., cyclopropyl, cyclobutyl, cyclopentyl, cyclohexyl) optionally fused with a benzene ring, (ii) an oxetanyl group, (iii) a tetrahydrofuranyl group, or (iv) a tetrahydropyranyl group, each of which is optionally further substituted by 1 to 3 substituents selected from (1) a halogen atom (e.g., fluorine atom), (2) a $C_{1-6}$ alkyl group (e.g., methyl) optionally substituted by 1 to 3 hydroxy groups, and (3) a $C_{1-6}$ alkoxy group (e.g., methoxy);

$R^1$ is a hydrogen atom or a hydroxyl group;

$R^2$ is a hydrogen atom, a $C_{1-6}$ alkyl group (e.g., methyl) or a $C_{1-6}$ alkoxy group (e.g., methoxy);

$R^3$ is a hydrogen atom, a halogen atom (e.g., fluorine atom, chlorine atom), a cyano group, a $C_{1-6}$ alkyl group (e.g., methyl, ethyl) optionally substituted by 1 to 3 halogen atoms (e.g., fluorine atom), a $C_{2-6}$ alkenyl group (e.g., vinyl), a $C_{3-6}$ cycloalkyl group (e.g., cyclopropyl), or a $C_{1-6}$ alkoxy group (e.g., methoxy) optionally substituted by 1 to 3 halogen atoms (e.g., fluorine atom);

$R^4$ is a hydrogen atom or a halogen atom (e.g., fluorine atom);

$R^5$ is a pyrazolyl group optionally substituted by 1 to 3 $C_{1-6}$ alkyl groups (e.g., methyl), a halogen atom (e.g., bromine atom), a cyano group, or a $C_{1-6}$ alkoxy group (e.g., methoxy); and X is CH.

[Compound I-7]

Compound (I) wherein

A is (i) a $C_{3-10}$ cycloalkyl group (e.g., cyclopentyl, cyclohexyl), or (ii) a tetrahydropyranyl group;

$R^1$ is a hydroxyl group;

$R^2$ is a hydrogen atom, or a $C_{1-6}$ alkyl group (e.g., methyl);

$R^3$ is a halogen atom (e.g., chlorine atom), a $C_{1-6}$ alkyl group (e.g., methyl), or a $C_{1-6}$ alkoxy group (e.g., methoxy);

$R^4$ is a hydrogen atom;

$R^5$ is a pyrazolyl group optionally substituted by 1 to 3 $C_{1-6}$ alkyl groups (e.g., methyl, ethyl), a halogen atom (e.g., chlorine atom), a cyano group, a $C_{1-6}$ alkyl group (e.g., methyl), or a $C_{1-6}$ alkoxy group (e.g., methoxy); and X is N.

[Compound I-8]
Compound (I) wherein
A is
(i) a $C_{3-10}$ cycloalkyl group (e.g., cyclopentyl, cyclohexyl), or
(ii) a tetrahydropyranyl group;
$R^1$ is a hydroxyl group;
$R^2$ is a hydrogen atom, or a $C_{1-6}$ alkyl group (e.g., methyl);
$R^3$ is a halogen atom (e.g., chlorine atom), a cyano group, a $C_{1-6}$ alkyl group (e.g., methyl), or a $C_{1-6}$ alkoxy group (e.g., methoxy);
$R^4$ is a hydrogen atom;
$R^5$ is a pyrazolyl group optionally substituted by 1 to 3 $C_{1-6}$ alkyl groups (e.g., methyl), or a halogen atom (e.g., chlorine atom); and
X is CH or N.

[Compound I-9]
Compound (I) wherein
A is
(i) a $C_{3-10}$ cycloalkyl group (e.g., cyclopentyl, cyclohexyl), or
(ii) a tetrahydropyranyl group;
$R^1$ is a hydroxyl group;
$R^2$ is a hydrogen atom, or a $C_{1-6}$ alkyl group (e.g., methyl);
$R^3$ is a halogen atom (e.g., chlorine atom), a cyano group, a $C_{1-6}$ alkyl group (e.g., methyl), or a $C_{1-6}$ alkoxy group (e.g., methoxy);
$R^4$ is a hydrogen atom;
$R^5$ is a pyrazolyl group optionally substituted by 1 to 3 $C_{1-6}$ alkyl groups (e.g., methyl); and
X is CH.

[Compound I-10]
Compound (I) wherein
A is a $C_{3-10}$ cycloalkyl group (e.g., cyclohexyl);
$R^1$ is a hydroxyl group;
$R^2$ is a $C_{1-6}$ alkyl group (e.g., methyl);
$R^3$ is a $C_{1-6}$ alkyl group (e.g., methyl);
$R^4$ is a hydrogen atom;
$R^5$ is a pyrazolyl group optionally substituted by 1 to 3 $C_{1-6}$ alkyl groups (e.g., methyl), or a halogen atom (e.g., chlorine atom); and
X is N.

[Compound I-11]
Compound (I) wherein
A is a $C_{3-10}$ cycloalkyl group (e.g., cyclopentyl, cyclohexyl);
$R^1$ is a hydroxyl group;
$R^2$ is a hydrogen atom, or a $C_{1-6}$ alkyl group (e.g., methyl);
$R^3$ is a $C_{1-6}$ alkyl group (e.g., methyl);
$R^4$ is a hydrogen atom;
$R^5$ is a pyrazolyl group optionally substituted by 1 to 3 $C_{1-6}$ alkyl groups (e.g., methyl); and
X is CH or N.

[Compound I-12]
Compound (I) wherein
A is a $C_{3-10}$ cycloalkyl group (e.g., cyclopentyl);
$R^1$ is a hydroxyl group;
$R^2$ is a hydrogen atom, or a $C_{1-6}$ alkyl group (e.g., methyl);
$R^3$ is a $C_{1-6}$ alkyl group (e.g., methyl);
$R^4$ is a hydrogen atom;
$R^5$ is a pyrazolyl group optionally substituted by 1 to 3 $C_{1-6}$ alkyl groups (e.g., methyl); and
X is CH.

[Compound I-13]
Compound (I) wherein
A is a $C_{3-10}$ cycloalkyl group (e.g., cyclohexyl);
$R^1$ is a hydroxyl group;
$R^2$ is a $C_{1-6}$ alkyl group (e.g., methyl);
$R^3$ is a $C_{1-6}$ alkyl group (e.g., methyl);
$R^4$ is a hydrogen atom;
$R^5$ is a pyrazolyl group optionally substituted by 1 to 3 $C_{1-6}$ alkyl groups (e.g., methyl); and
X is N.

Specific examples of compound (I) include the compounds of Examples 1-2 and 4-117 and, of these,
N-((1S,2S)-2-hydroxycyclopentyl)-5-methyl-4-(4-(1-methyl-1H-pyrazol-3-yl)benzyl)pyridine-2-carboxamide (Example 1);
N-((1S,2S)-2-hydroxycyclopentyl)-5,6-dimethyl-4-(4-(1-methyl-1H-pyrazol-3-yl)benzyl)pyridine-2-carboxamide (Example 72); and
N-((1S,2S)-2-hydroxycyclohexyl)-5,6-dimethyl-4-((6-(1-methyl-1H-pyrazol-3-yl)pyridin-3-yl)methyl)pyridine-2-carboxamide (Example 74);
are preferable.

When compound (I) is in the form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, examples of a preferable pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. compound (I) may be a compound labeled or substituted with an isotope (e.g., $^2$H, $^3$H, $^{11}$C, $^{14}$C, $^{18}$F, $^{35}$S, $^{125}$I). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are also encompassed in compound (I) of the present invention.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature-300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate, tert-butylcarbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride, a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., basic salts, organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1'-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound, iridium compound and the like. A base may be further added to the reaction and examples of such base include inorganic bases, basic salts and the like.

When a coupling reaction is performed in each step, examples of the metal catalyst to be used also include palladium compounds such as trans-di(mu-acetato)bis[o-(di-o-tolylphosphino)benzyl]dipalladium(II) and the like; iridium compounds such as di-mu-methoxobis(1,5-cyclooctadiene)diiridium(I) and the like, and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid, phosphorus tribromide and the like for bromination. In addition, a method of obtaining an alkyl halide form from alcohol by reacting with triphenylphosphine and carbon tetrachloride or carbon tetrabromide, and the like may be used. Alternatively, a method of synthesizing a alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonic acid esterification reaction is performed in each step, examples of the sulfonylating agent to be used include methanesulfonyl chloride, p-toluenesulfonyl chloride, methanesulfonic anhydride, p-toluenesulfonic anhydride and the like.

When hydrolysis reaction is performed in each step, an acid or a base is used as the reagent. In addition, when acid hydrolysis reaction of t-butyl ester is performed, formic acid, triethylsilane and the like are sometimes added to reductively trap the by-produced t-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Compound (I) can be produced from compound (1) by the following method.

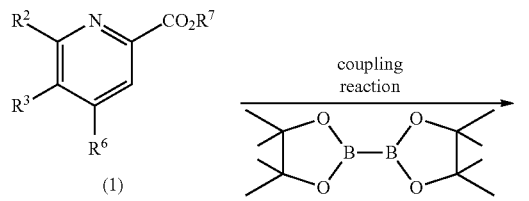

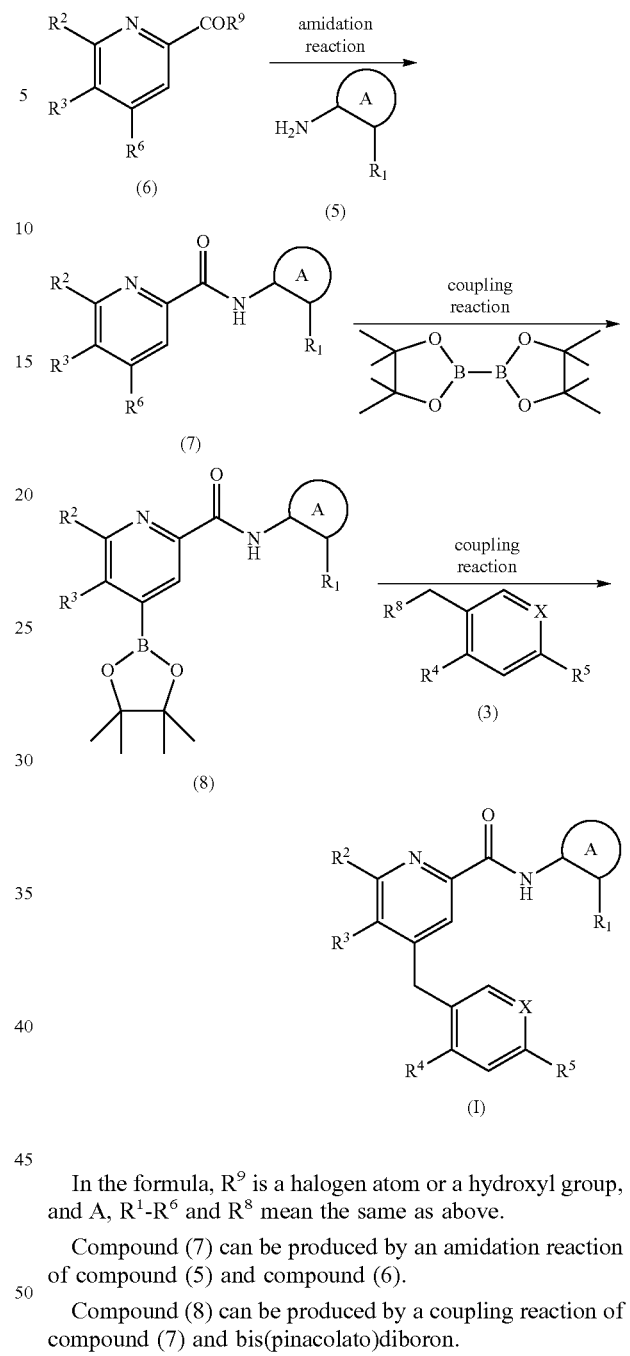

In the formula, $R^6$ is a hydrogen atom or a halogen atom, $R^7$ is a lower alkyl group, $R^8$ is a halogen atom, and A and $R^1$-$R^5$ mean the same as above.

Compound (2) can be produced by a coupling reaction of compound (1) and bis(pinacolato)diboron.

Compound (4) can be produced by a coupling reaction of compound (2) and compound (3).

Compound (I) can be produced by hydrolysis reaction of compound (4) and a successive amidation reaction with compound (5).

Compound (I) can also be produced from compound (6) by the following method.

In the formula, $R^9$ is a halogen atom or a hydroxyl group, and A, $R^1$-$R^6$ and $R^8$ mean the same as above.

Compound (7) can be produced by an amidation reaction of compound (5) and compound (6).

Compound (8) can be produced by a coupling reaction of compound (7) and bis(pinacolato)diboron.

Compound (I) can be produced by a coupling reaction of compound (3) and compound (8).

Compound (4) can also be produced from compound (9) by the following method.

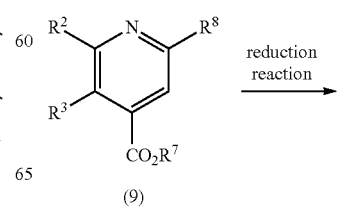

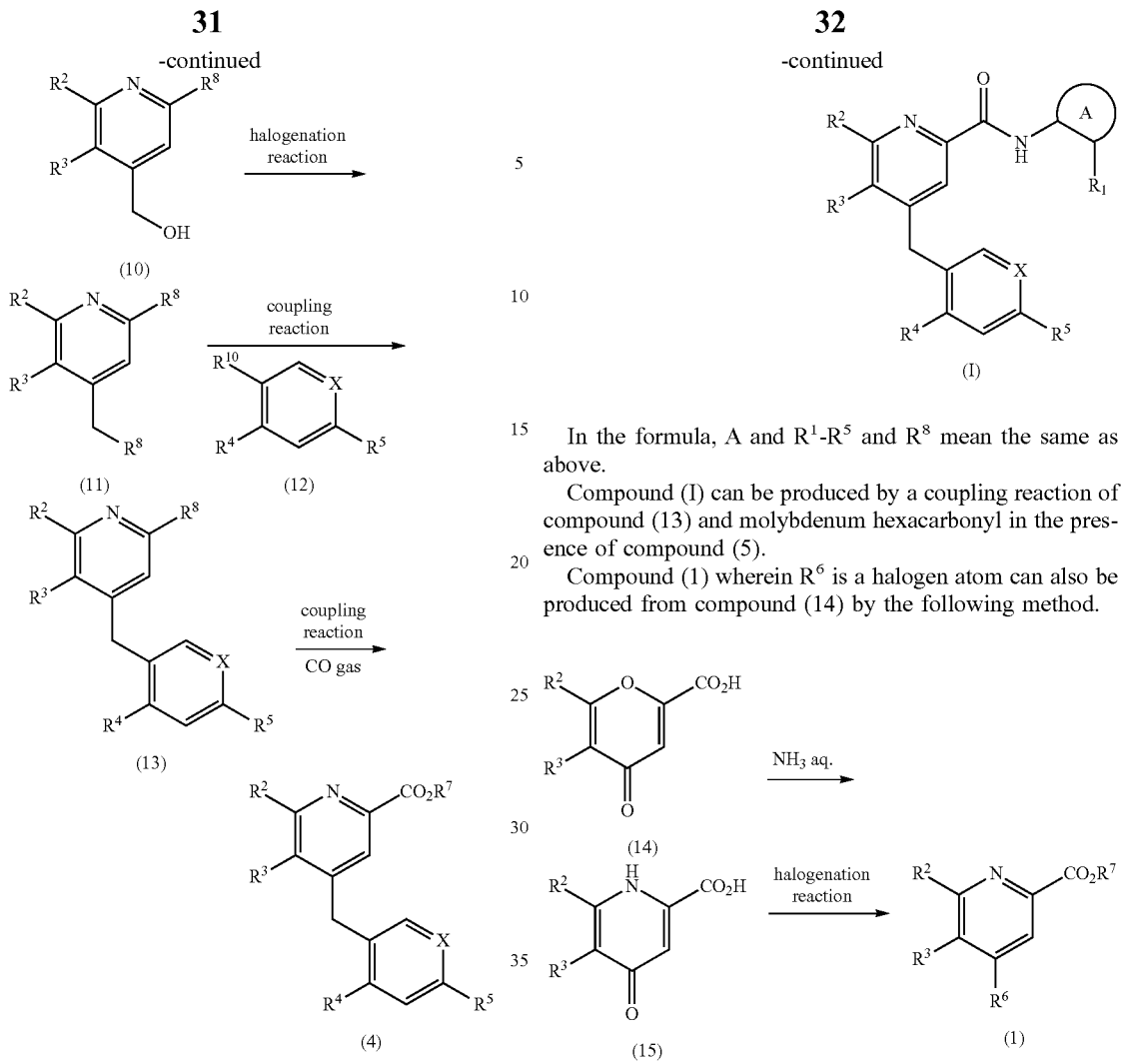

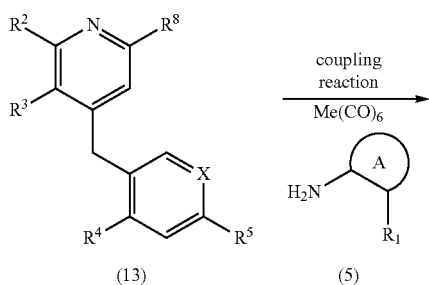

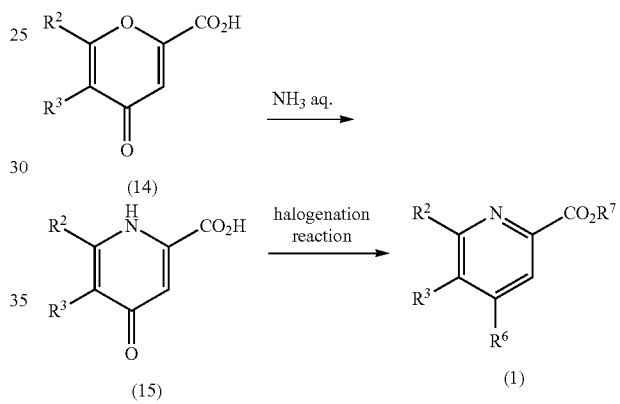

In the formula, $R^{10}$ is boronic acid or boronic acid ester, and A, $R^2$-$R^5$ and $R^7$-$R^9$ mean the same as above.

Compound (10) can be produced by a reduction reaction of compound (9).

Compound (11) can be produced by a halogenation reaction of compound (10).

Compound (13) can be produced by a coupling reaction of compound (11) and compound (12).

Compound (4) can be produced by a coupling reaction of compound (13) and carbon monoxide in the presence of alcohol represented by the formula: $R^7$—OH.

Compound (I) can also be produced from compound (13) by the following method.

In the formula, A and $R^1$-$R^5$ and $R^8$ mean the same as above.

Compound (I) can be produced by a coupling reaction of compound (13) and molybdenum hexacarbonyl in the presence of compound (5).

Compound (1) wherein $R^6$ is a halogen atom can also be produced from compound (14) by the following method.

In the formula, A, $R^2$-$R^3$ and $R^6$-$R^7$ mean the same as above.

Compound (15) can be produced by a reaction of compound (14) with aqueous ammonia.

Compound (1) can be produced by a halogenation reaction of compound (15) and a successive esterification reaction.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series manufactured by Daicel Corporation and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, t-butylation and the like); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be a crystal, and a single crystal form and a mixture of crystal forms are both encompassed in compound (I) of the present invention. The crystal can be produced by crystallizing according to a crystallization method known per se.

Compound (I) is effective for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autism spectrum syndrome, fragile X syndrome, Rett syndrome, adjustment disorder, bipolar disorder, neurosis, schizophrenia (e.g., positive symptom, negative symptom, cognitive impairment), cognitive dysfunction associated with schizophrenia, chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Parkinson's disease dementia, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, post-encephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, multiple sclerosis], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, peptic ulcer, diarrhea, constipation, postoperative ileus, (7) pain and the like. compound (I) is particularly preferably effective as a cholinergic muscarinic M1 receptor positive allosteric modulator, a prophylactic or therapeutic drug for Alzheimer's disease, schizophrenia, pain, sleep disorder, Parkinson's disease dementia, dementia with Lewy bodies and the like.

Since compound (I) has an excellent cholinergic muscarinic M1 receptor positive allosteric modulator activity, it is expected to provide an excellent prophylactic or therapeutic effect for the above-mentioned diseases.

Since compound (I) is excellent in solubility in water, the Japanese Pharmacopoeia dissolution test 2nd fluid, or the Japanese Pharmacopoeia disintegration test 2nd fluid, excellent in pharmacokinetics (e.g., plasma drug half-life, intracerebral migration, metabolic stability, CYP inhibition), shows low toxicity (e.g., more excellent as a medicament in terms of acute toxicity, chronic toxicity, genetic toxicity, reproductive toxicity, cardiotoxicity, drug interaction, carcinogenicity, phototoxicity and the like), and also has excellent properties as a pharmaceutical product such as a few side effects and the like, it can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A preparation containing compound (I) may be any of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the preparation of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation.

When compound (I) is used as the above-mentioned pharmaceutical products, it may be used alone or in admixture with a suitable, pharmacologically acceptable carrier, for example, excipients (e.g., starch, lactose, white soft sugar, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and administered orally or parenterally. When compound (I) is formed as a preparation for topical administration, it can also be directly administered to the affected part of an articular disease. In this case, an injection is preferable. The compound can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain fatty acid triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with Alzheimer's disease, the dose is, for example, 0.001 to 1000 mg/kg body weight/day, preferably 0.01 to 100 mg/kg body weight/day, more preferably 0.1 to 10 mg/kg body weight/day, as compound (I). This amount can be administered in one to three portions per day.

A medicament containing the compound of the present invention may be able to use the compound of the present invention solely or as a pharmaceutical composition of the compound of the present invention mixed with a pharmaceutically acceptable carrier according to a method known per se (e.g., the method described in the Japanese Pharmacopoeia etc.) as the production method of a pharmaceutical preparation. The medicament containing the compound of the present invention may be able to be administered safely in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal, lesion and the like).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like can also be used.

Examples of the excipient include lactose, white soft sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white soft sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphate salts, acetate salts, carbonate salts, citrate salts and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salts, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT$_{1A}$ agonist (buspirone hydrochloride, tandospirone citrate, osemozotan hydrochloride etc.), 5-HT$_3$ antagonist (cyamemazine etc.), heart non-selective β inhibitor (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for. Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination of those drugs etc.), therapeutic drug for Parkinson's disease dementia (rivastigmine), therapeutic drug for dementia with Lewy bodies (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, anti-obesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of the administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent in the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, a suitable amount of conventional preservative, antioxidant, colorant, sweetening agent, adsorbent, wetting agent and the like can be used as appropriate.

Examples of the excipient include lactose, white soft sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white soft sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphate salts, acetate salts, carbonate salts, citrate salts and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salts, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In Examples below, the following abbreviations are used.
THF: tetrahydrofuran
DMF: N,N-dimethylformamide
DME: 1,2-dimethoxyethane
DMSO: dimethyl sulfoxide
ESI: electrospray ionization method
APCI: atmospheric pressure chemical ionization
[M+H]$^+$: molecular ion peak
M: mol concentration
HPLC: high performance liquid chromatography
TFA: trifluoroacetic acid
DBU: 1,8-diazabicyclo[5.4.0]undec-7-ene
CDI: 1,1'-carbonyldiimidazole
WSC: 1-ethyl-3-(3-dimethylaminopropyl)carbodiimide hydrochloride
HOBt: 1-hydroxybenzotriazole
DIPEA: diisopropylethylamine
DMAP: N,N-dimethyl-4-aminopyridine
Pd(Ph$_3$P)$_4$: tetrakistriphenylphosphine
Pd(dppf)Cl$_2$ DCM: [1,1'-bis(diphenylphosphino)ferrocene]dichloropalladium(II), dichloromethane adduct
(Ph$_3$P)$_2$PdCl$_2$: trans-dichlorobis(triphenylphosphine)palladium(II)
Pd$_2$(dba)$_3$: tris(dibenzylideneacetone)dipalladium(0)
X-phos: 2-dicyclohexylphosphino-2',4',6'-triisopropylbiphenyl
$^1$H NMR (proton nuclear magnetic resonance spectrum) was measured by Fourier-transform NMR. For the analysis, ACD/SpecManager (trade name) and the like were used. Very mild peaks for protons of a hydroxy group, an amino group and the like are not described.

MS (mass spectrum) was measured by LC/MS (liquid chromatograph mass spectrometer). As ionization, ESI (Electro Spray Ionization) method, or APCI (Atmospheric Pressure Chemical Ionization) method was used. The data indicates those found. Generally, molecular ion peaks are observed. When a compound having a tert-butoxycarbonyl group (—Boc) is used, a peak free of a tert-butoxycarbonyl group or a tert-butyl group may be observed as a fragment ion. In addition, when a compound having a hydroxyl group (—OH) is used, a peak free of H$_2$O may be observed as a fragment ion. In the case of a salt, generally, a molecular ion peak or a fragment ion peak of a free form is observed.

Example 1

N-((1S,2S)-2-hydroxycyclopentyl)-5-methyl-4-(4-(1-methyl-1H-pyrazol-3-yl)benzyl)pyridine-2-carboxamide A) (4-(1-methyl-1H-pyrazol-3-yl)phenyl)methanol 4-(Hydroxymethyl)phenylboronic acid (3.68 g), 3-bromo-1-methyl-1H-pyrazole (3.00 g), sodium carbonate (4.54 g) and Pd(dppf)Cl$_2$ DCM (1.97 g) were heated under reflux in a mixture of toluene (60 mL), ethanol (10 mL) and water (10 mL) under a nitrogen atmosphere for 16 hr. The reaction mixture was cooled to room temperature and diluted with ethyl acetate, and the organic layer was washed with water (twice) and saturated brine, and dried over anhydrous sodium sulfate. The solvent was evaporated under reduced pressure. The residue was purified by silica gel column chromatography (ethyl acetate/petroleum ether) to give the title compound (2.30 g).

¹H NMR (400 MHz, CDCl₃) δ2.06 (1H, t, J=5.6 Hz), 3.97 (3H, s), 4.72 (2H, d, J=5.2 Hz), 6.56 (1H, d, J=2.4 Hz), 7.38-7.41 (3H, m), 7.79 (2H, d, J=8.4 Hz).

B) 3-(4-(bromomethyl)phenyl)-1-methyl-1H-pyrazole

To a solution of (4-(1-methyl-1H-pyrazol-3-yl)phenyl)methanol (2.30 g) in dichloromethane (50 mL) was added dropwise under ice-cooling phosphorus tribromide (9.93 g), and the mixture was stirred under a nitrogen atmosphere at 0° C. for 1 hr. The reaction mixture was added to saturated aqueous sodium carbonate solution under ice-cooling, and the organic layer was separated. Furthermore, the aqueous layer was extracted twice with dichloromethane, and the combined organic layer was dried over anhydrous sodium sulfate. The solvent was evaporated under reduced pressure. The residue was purified by silica gel column chromatography (ethyl acetate/petroleum ether) to give the title compound (1.25 g).

¹H NMR (400 MHz, CDCl₃) δ3.95 (3H, s), 4.53 (2H, s), 6.53 (1H, d, J=2.4 Hz), 7.38 (1H, d, J=2.4 Hz), 7.41 (2H, d, J=8.0 Hz), 7.76 (2H, d, J=8.4 Hz).

C) methyl 4-chloro-5-methylpicolinate

To a mixture of 5-methylpicolinic acid (13.7 g) and thionyl chloride (150 mL) was added sodium bromide (20.6 g) by small portions, and the mixture was heated under reflux under a nitrogen atmosphere for 1 hr. DMF (2 mL) was added and the mixture was further heated under reflux under a nitrogen atmosphere for 16 hr. An operation to add toluene (100 mL) to the reaction mixture and evaporate the solvent under reduced pressure was repeated twice, and toluene (100 mL) was added to the obtained residue. To a mixture thereof were added DIPEA (25.8 g) and methanol (20 mL) under a nitrogen atmosphere at 0° C., and the mixture was further stirred at 20° C. for 2 hr. The solvent was evaporated under reduced pressure and the obtained residue was purified by silica gel column chromatography (ethyl acetate/petroleum ether) to give the title compound (9.40 g).

¹H NMR (400 MHz, CDCl₃) δ2.43 (3H, s), 3.99 (3H, s), 8.10 (1H, s), 8.54 (1H, s).

D) methyl 5-methyl-4-(4,4,5,5-tetramethyl-1,3,2-dioxaborolan-2-yl)picolinate Methyl 4-chloro-5-methylpicolinate (8.75 g), bis(pinacolato)diboron (17.9 g), Pd₂(dba)₃ (4.31 g), X-phos (4.48 g) and potassium acetate (13.8 g) were stirred in 1,4-dioxane (200 mL) under a nitrogen atmosphere at 65° C. for 32 hr. The solvent was evaporated under reduced pressure, and the obtained residue was purified by silica gel column chromatography (ethyl acetate/petroleum ether) to give the title compound (11.5 g, containing bis(pinacolato)diboron).

¹H NMR (400 MHz, CDCl₃) δ1.36 (12H, s), 2.56 (3H, s), 3.99 (3H, s), 8.39 (1H, s), 8.55 (1H, s).

E) methyl 5-methyl-4-(4-(1-methyl-1H-pyrazol-3-yl)benzyl)picolinate

Methyl 5-methyl-4-(4,4,5,5-tetramethyl-1,3,2-dioxaborolan-2-yl)picolinate (4.17 g, containing bis(pinacolato)diboron), 3-(4-(bromomethyl)phenyl)-1-methyl-1H-pyrazole (3.17 g), potassium carbonate (2.93 g) and Pd(dppf)Cl₂ DCM (0.737 g) were stirred in a mixture of toluene (60 mL), 1,4-dioxane (6 mL) and water (6 mL) under a nitrogen atmosphere at 60° C. for 16 hr. The reaction mixture was concentrated under reduced pressure, and the obtained residue was purified by silica gel column chromatography (ethyl acetate/petroleum ether) to give the title compound (2.76 g).

¹H NMR (400 MHz, CDCl₃) δ2.31 (3H, s), 3.94 (3H, s), 3.97 (3H, s), 4.03 (2H, s), 6.50 (1H, d, J=2.0 Hz), 7.12 (2H, d, J=8.0 Hz), 7.36 (1H, d, J=2.4 Hz), 7.72 (2H, d, J=8.4 Hz), 7.91 (1H, s), 8.49 (1H, s).

F) 5-methyl-4-(4-(1-methyl-1H-pyrazol-3-yl)benzyl)picolinic Acid

Methyl 5-methyl-4-(4-(1-methyl-1H-pyrazol-3-yl)benzyl)picolinate (1.75 g) and lithium hydroxide monohydrate (0.916 g) were stirred in a mixture of THF (20 mL) and water (10 mL) at 20° C. for 16 hr. The reaction mixture was extracted 5 times with ethyl acetate/methanol, and the aqueous layer was neutralized with saturated aqueous citric acid solution and extracted 10 times with dichloromethane/methanol. The combined organic layer was dried over anhydrous sodium sulfate, and the solvent was evaporated under reduced pressure to give the title compound (1.60 g).

¹H NMR (400 MHz, DMSO-d₆) δ2.31 (3H, s), 3.86 (3H, s), 4.06 (2H, s), 6.65 (1H, d, J=2.0 Hz), 7.19 (2H, d, J=8.0 Hz), 7.70-7.75 (4H, m), 8.45 (1H, s) (* peak of one "COOH group" was not observed).

G) N-((1S,2S)-2-hydroxycyclopentyl)-5-methyl-4-(4-(1-methyl-1H-pyrazol-3-yl)benzyl)pyridine-2-carboxamide 5-Methyl-4-(4-(1-methyl-1H-pyrazol-3-yl)benzyl)picolinic acid (507 mg), (1S,2S)-2-aminocyclopentanol hydrochloride (454 mg), WSC (632 mg), HOBt (446 mg) and triethylamine (334 mg) were stirred in DMF (20 mL) under a nitrogen atmosphere at room temperature overnight. To the reaction mixture were added water and triethylamine (1 mL), and the mixture was extracted 4 times with ethyl acetate. The obtained organic layer was washed with saturated brine, dried over anhydrous sodium sulfate, and the solvent was evaporated under reduced pressure. The residue was purified by silica gel column chromatography (ethyl acetate/methanol) and crystallized from ethyl acetate-hexane to give the title compound (537 mg).

¹H NMR (300 MHz, CDCl₃) δ 1.61-1.92 (4H, m), 2.04-2.16 (1H, m), 2.18-2.27 (1H, m), 2.29 (3H, s), 3.94 (3H, s), 3.96-4.02 (1H, m), 4.04 (2H, s), 4.07-4.18 (1H, m), 4.60 (1H, d, J=1.5 Hz), 6.50 (1H, d, J=2.3 Hz), 7.13 (2H, d, J=8.1 Hz), 7.36 (1H, d, J=2.3 Hz), 7.70 (2H, d, J=8.1 Hz), 8.00 (1H, s), 8.11 (1H, d, J=3.0 Hz), 8.28 (1H, s).

Example 2

1,5-anhydro-2,4-dideoxy-2-(((5-methyl-4-(4-(1-methyl-1H-pyrazol-3-yl)benzyl)pyridin-2-yl)carbonyl)amino)-L-threo-pentitol 5-Methyl-4-(4-(1-methyl-1H-pyrazol-3-yl)benzyl)picolinic acid (200 mg), (3S,4S)-2-aminotetrahydro-2H-pyran-4-ol (91.0 mg), WSC (162 mg) and HOBt monohydrate (100 mg) were stirred in DMF (5 mL) at room temperature overnight. The reaction mixture was diluted with water and extracted with ethyl acetate. The obtained organic layer was washed with water, dried over anhydrous magnesium sulfate, and the solvent was evaporated under reduced pressure. The residue was purified by silica gel column chromatography (ethyl acetate/hexane-ethyl acetate/methanol) to give the title compound (200 mg).

$^1$H NMR (300 MHz, CDCl$_3$) δ1.66-1.84 (1H, m), 2.00-2.16 (1H, m), 2.28 (3H, s), 3.32 (1H, brs), 3.33-3.43 (1H, m), 3.45-3.58 (1H, m), 3.76-3.89 (1H, m), 3.94 (3H, s), 3.95-4.02 (2H, m), 4.04 (2H, s), 4.13 (1H, dd, J=11.1, 4.2 Hz), 6.49 (1H, d, J=2.3 Hz), 7.12 (2H, d, J=8.4 Hz), 7.36 (1H, d, J=2.3 Hz), 7.60-7.78 (2H, m), 8.00 (1H, s), 8.12 (1H, d, J=7.2 Hz), 8.28 (1H, s)

Example 4

N-(trans-2-hydroxycyclohexyl)-5-methyl-4-(4-(1H-pyrazol-1-yl)benzyl)pyridine-2-carboxamide A) 4-chloro-N-(trans-2-hydroxycyclohexyl)-5-methylpicolinamide To thionyl chloride (45 mL) were added under ice-cooling 5-methylpicolinic acid (15.0 g), and further DMF (1.5 mL), and the mixture was stirred under a nitrogen atmosphere at 90° C. for 16 hr. An operation to add toluene (120 mL) to the reaction mixture and evaporate the solvent under reduced pressure was repeated twice. To the obtained residue was added dichloromethane (100 mL). To a mixture thereof were added triethylamine (22.0 g) and trans-2-aminohexanol hydrochloride (19.8 g) under a nitrogen atmosphere at 0° C., and the mixture was further stirred at 14° C. for 16 hr. The reaction mixture was filtered, an insoluble material was washed with dichloromethane, and the obtained organic layer was washed with saturated brine, dried over anhydrous sodium sulfate, and the solvent was evaporated under reduced pressure. The residue was purified by silica gel column chromatography (ethyl acetate/petroleum ether) to give the title compound (5.90 g).

$^1$H NMR (400 MHz, DMSO-d$_6$) δ1.30-1.47 (4H, m), 1.75-1.80 (2H, m), 2.05-2.14 (2H, m), 2.42 (3H, s), 3.37 (1H, brs), 3.46-3.52 (1H, m), 3.78-3.87 (1H, m), 7.93 (1H, d, J=6.8 Hz), 8.16 (1H, s), 8.35 (1H, s).

B) N-(trans-2-hydroxycyclohexyl)-5-methyl-4-(4,4,5,5-tetramethyl-1,3,2-dioxaborolan-2-yl)picolinamide 4-Chloro-N-(trans-2-hydroxycyclohexyl)-5-methylpicolinamide (900 mg), bis(pinacolato)diboron (1.11 g), potassium acetate (986 mg), dppf (93.0 mg) and Pd(dppf)Cl$_2$ DCM (137 mg) were stirred in 1,4-dioxane (30 mL) under a nitrogen atmosphere at 90° C. for 16 hr. To the reaction mixture was added ethyl acetate, and the obtained organic layer was washed with saturated brine, dried over anhydrous sodium sulfate, and the solvent was evaporated under reduced pressure. The residue was purified by silica gel column chromatography (ethyl acetate/petroleum ether) to give the title compound (224 mg).

$^1$H NMR (400 MHz, CDCl$_3$) δ1.33-1.45 (16H, m), 1.76-1.80 (2H, m), 2.09-2.12 (2H, m), 2.56 (3H, s), 3.45-3.55 (1H, m), 3.80-3.92 (2H, m), 8.00 (1H, d, J=7.6 Hz), 8.36 (1H, s), 8.48 (1H, s).

C) N-(trans-2-hydroxycyclohexyl)-5-methyl-4-(4-(1H-pyrazol-1-yl)benzyl)pyridine-2-carboxamide N-(trans-2-hydroxycyclohexyl)-5-methyl-4-(4,4,5,5-tetramethyl-1,3,2-dioxaborolan-2-yl)picolinamide (224 mg), 1-[4-(chloromethyl)phenyl]-1H-pyrazole (125 mg), tripotassium phosphate trihydrate (330 mg) and Pd(dppf)Cl$_2$ DCM (25.0 mg) were stirred in a mixed solution of 1,4-dioxane (10 mL) and water (1 mL) under a nitrogen atmosphere at 80° C. for 16 hr. To the reaction mixture was added ethyl acetate, and the obtained organic layer was washed with saturated brine, dried over anhydrous sodium sulfate, and the solvent was evaporated under reduced pressure. The residue was purified by silica gel column chromatography (ethyl acetate/petroleum ether) to give the title compound (49.0 mg).

Example 6

5-chloro-N-((1S,2S)-2-hydroxycyclohexyl)-4-(4-(1H-pyrazol-1-yl)benzyl)pyridine-2-carboxamide A) (2,5-dichloropyridin-4-yl)methanol To a solution of methyl 2,5-dichloroisonicotinate (2.25 g) in THF (50 mL) was added sodium borohydride (0.828 g), ethanol (20 mL) was added dropwise, and the mixture was stirred at 50° C. for 4 hr. To the reaction mixture was added 1 M aqueous hydrochloric acid solution. The solvent was evaporated under reduced pressure, and the obtained residue was diluted with water, and the mixture was extracted with ethyl acetate. The obtained organic layer was washed with saturated brine, dried over anhydrous magnesium sulfate, and the solvent was evaporated under reduced pressure to give the title compound (1.90 g).

MS (ESI+): [M+H]$^+$ 177.8.

B) 4-(bromomethyl)-2,5-dichloropyridine

To a solution of (2,5-dichloropyridin-4-yl)methanol (4.80 g) in acetonitrile (100 mL) was added dropwise phosphorus tribromide (8.03 g) at 0° C., and the mixture was stirred under a nitrogen atmosphere at 0° C. for 2 hr. To the reaction mixture was added saturated aqueous sodium carbonate solution under ice-cooling, and the mixture was extracted with ethyl acetate. The obtained organic layer was washed with water, dried over anhydrous magnesium sulfate, and the solvent was evaporated under reduced pressure. The residue was purified by silica gel column chromatography (ethyl acetate/hexane) to give the title compound (3.40 g).

$^1$H NMR (400 MHz, CDCl$_3$) δ4.45 (2H, s), 7.43 (1H, s), 8.38 (1H, s).

C) 1-(4-bromophenyl)-1H-pyrazole

To a solution of 1-bromo-4-fluorobenzene (10.0 g) and 1H-pyrazole (3.89 g) in DMF (100 mL) was added under ice-cooling sodium hydride (2.29 g, 60%, oily), and the mixture was stirred at room temperature for 30 min and further at 130° C. for 5 hr. To the reaction mixture was added water, and the mixture was extracted with ethyl acetate. The organic layer was washed with water, dried over anhydrous magnesium sulfate and the solvent was evaporated under reduced pressure to give the title compound (13.0 g).

MS (ESI+): [M+H]$^+$ 222.8.

D) 1-(4-(4,4,5,5-tetramethyl-1,3,2-dioxaborolan-2-yl)phenyl)-1H-pyrazole

To a solution of 1-(4-bromophenyl)-1H-pyrazole (12.8 g), bis(pinacolato)diboron (29.0 g), potassium acetate (16.8 g) in toluene (300 mL) was added (Ph$_3$P)$_2$PdCl$_2$ (4.01 g), and the mixture was stirred under an argon atmosphere at 110° C. overnight. An insoluble material was removed by filtration, and the solvent was evaporated under reduced pressure. The obtained residue was purified by silica gel column chromatography (ethyl acetate/hexane) to give the title compound (13.2 g, containing bis(pinacolato)diboron).
MS (ESI+): [M+H]$^+$ 271.0.

E) 4-(4-(1H-pyrazol-1-yl)benzyl)-2,5-dichloropyridine

To a solution of 4-(bromomethyl)-2,5-dichloropyridine (800 mg) and 1-(4-(4,4,5,5-tetramethyl-1,3,2-dioxaborolan-2-yl)phenyl)-1H-pyrazole (897 mg) in DME (30 mL) were added Pd(Ph$_3$P)$_4$ (384 mg) and 2 M aqueous sodium carbonate solution (12 mL), and the mixture was stirred under an argon atmosphere at 100° C. overnight. To the reaction mixture was added water, and the mixture was extracted with ethyl acetate. The obtained organic layer was washed with water, dried over anhydrous magnesium sulfate, and the solvent was evaporated under reduced pressure. The residue was purified by silica gel column chromatography (ethyl acetate/hexane) to give the title compound (480 mg).
MS (ESI+): [M+H]$^+$ 303.9.

F) methyl 4-(4-(1H-pyrazol-1-yl)benzyl)-5-chloropicolinate 4-(4-(1H-pyrazol-1-yl)benzyl)-2,5-dichloropyridine (480 mg), Pd(dppf)Cl$_2$ DCM (129 mg) and triethylamine (160 mg) were stirred in a mixed solution of methanol (5 mL) and DMF (5 mL) in the presence of carbon monoxide (3 atm) at 80° C. for 5 hr. The solvent of the reaction mixture was evaporated under reduced pressure, and the obtained residue was purified by silica gel column chromatography (ethyl acetate/hexane) to give the title compound (440 mg).
MS (ESI+): [M+H]$^+$ 327.9.

G) 4-(4-(1H-pyrazol-1-yl)benzyl)-5-chloropicolinic Acid

Methyl 4-(4-(1H-pyrazol-1-yl)benzyl)-5-chloropicolinate (500 mg), 2 M aqueous sodium hydroxide solution (3.1 mL) were stirred in a mixed solution of THF (40 mL) and methanol (40 mL) at 60° C. for 1 hr. The reaction mixture was cooled to room temperature, 2 M hydrochloric acid (6.1 mL) was added to the reaction mixture, and the solvent was evaporated under reduced pressure to give the title compound. This was used for the next step without further purification.

H) 5-chloro-N-((1S,2S)-2-hydroxycyclohexyl)-4-(4-(1H-pyrazol-1-yl)benzyl)pyridine-2-carboxamide To a mixture of 4-(4-(1H-pyrazol-1-yl)benzyl)-5-chloropicolinic acid obtained in the previous step, (1S,2S)-2-aminocyclohexanol hydrochloride (278 mg), WSC (381 mg), and HOBt monohydrate (234 mg) in DMF (15 mL) was added triethylamine (464 mg), and the mixture was stirred at room temperature overnight. The reaction mixture was diluted with water, and extracted with ethyl acetate. The obtained organic layer was washed with water, dried over anhydrous magnesium sulfate, and the solvent was evaporated under reduced pressure. The residue was purified by silica gel column chromatography (ethyl acetate/hexane) to give the title compound (420 mg).
$^1$H NMR (300 MHz, CDCl$_3$) δ1.18-1.49 (4H, m), 1.68-1.87 (2H, m), 1.96-2.21 (2H, m), 3.24 (1H, d, J=4.3 Hz), 3.38-3.58 (1H, m), 3.66-3.89 (1H, m), 4.13 (2H, s), 6.45 (1H, dd, J=2.1, 1.8 Hz), 7.26-7.30 (2H, m), 7.54-7.66 (2H, m), 7.71 (1H, d, J=1.4 Hz), 7.89 (1H, dd, J=2.5, 0.5 Hz), 7.92 (1H, brs), 8.05 (1H, s), 8.48 (1H, s).

Example 8

1,5-anhydro-2-(((5-chloro-4-(4-(1H-pyrazol-1-yl)benzyl)pyridin-2-yl)carbonyl)amino)-2,4-dideoxy-L-threo-pentitol Hydrochloride A) 1,5-anhydro-2-(((5-chloro-4-(4-(1H-pyrazol-1-yl)benzyl)pyridin-2-yl)carbonyl)amino)-2,4-dideoxy-L-threo-pentitol The title compound was obtained by a method similar to that in Example 6, Step H. This was used for the next step without further purification.
MS (ESI+): [M+H]$^+$ 413.0.

B) 1,5-anhydro-2-(((5-chloro-4-(4-(1H-pyrazol-1-yl)benzyl)pyridin-2-yl) carbonyl)amino)-2,4-dideoxy-L-threo-pentitol Hydrochloride To a solution of 1,5-anhydro-2-(((5-chloro-4-(4-(1H-pyrazol-1-yl)benzyl)pyridin-2-yl)carbonyl)amino)-2,4-dideoxy-L-threo-pentitol obtained in the previous step in ethyl acetate (10 mL) was added 4 M hydrochloric acid/ethyl acetate solution (2 mL), and the mixture was stirred at room temperature for 2 hr. The obtained solid was collected by filtration and further recrystallized from ethanol to give the title compound (219 mg).

Example 10

4-(2-fluoro-4-(1-methyl-1H-pyrazol-3-yl)benzyl)-N-((1S,2S)-2-hydroxycyclohexyl)-5-methylpyridine-2-carboxamide A) methyl 2-fluoro-4-(1-methyl-1H-pyrazol-3-yl)benzoate 3-Fluoro-4-methoxycarbonylphenylboronic acid (24.5 g), 3-bromo-1-methyl-1H-pyrazole (13.3 g), sodium carbonate (21.9 g) and Pd(dppf)Cl$_2$ DCM (6.74 g) were heated under reflux in a mixture of toluene (200 mL), methanol (40 mL) and water (40 mL) under a nitrogen atmosphere for 16 hr. The reaction mixture was cooled to room temperature, ethyl acetate was added, and the obtained organic layer was washed with water and saturated brine, dried over anhydrous sodium sulfate, and the solvent was evaporated under reduced pressure. The residue was purified by silica gel column chromatography (ethyl acetate/petroleum ether) to give the title compound (12.5 g).
$^1$H NMR (400 MHz, CDCl$_3$) δ3.95 (3H, s), 3.98 (3H, s), 6.60 (1H, d, J=2.0 Hz), 7.43 (1H, d, J=2.4 Hz), 7.54-7.65 (2H, m), 7.95-8.00 (1H, m).

B) (2-fluoro-4-(1-methyl-1H-pyrazol-3-yl)phenyl)methanol

To a solution of methyl 2-fluoro-4-(1-methyl-1H-pyrazol-3-yl)benzoate (11.5 g) in THF (150 mL) were added calcium chloride (16.4 g), and then sodium borohydride (3.74 g) at 0° C., and the mixture was stirred under a nitrogen atmosphere at room temperature for 16 hr. To the reaction mixture were added calcium chloride (8.20 g) and sodium borohydride (1.82 g), and the mixture was further stirred for 6 hr.

The reaction mixture was added to saturated aqueous ammonium chloride solution, and the mixture was extracted with ethyl acetate. The obtained organic layer was washed with saturated brine, dried over anhydrous sodium sulfate, and the solvent was evaporated under reduced pressure. The residue was purified by silica gel column chromatography (ethyl acetate/petroleum ether) to give the title compound (9.00 g).

$^1$H NMR (400 MHz, CDCl$_3$) δ2.44 (1H, brs), 3.96 (3H, s), 4.76 (2H, s), 6.53 (1H, d, J=2.4 Hz), 7.38-7.55 (4H, m).

C) 4-(2-fluoro-4-(1-methyl-1H-pyrazol-3-yl)benzyl)-N-((1S,2S)-2-hydroxycyclohexyl)-5-methylpyridine-2-carboxamide The title compound was obtained by a method similar to that in Example 1, Steps B-G.

Example 12

4-(2-fluoro-4-(1H-pyrazol-1-yl)benzyl)-N-((1S,2S)-2-hydroxycyclohexyl)-5-methylpyridine-2-carboxamide A) methyl 2-fluoro-4-(1H-pyrazol-1-yl)benzoate Methyl 2,4-difluorobenzoate (20.0 g), pyrazole (7.92 g) and potassium carbonate (16.1 g) were stirred in DMSO (250 mL) at 60° C. for 16 hr. The reaction mixture was added to water, and the mixture was extracted with ethyl acetate. The obtained organic layer was washed with water, dried over anhydrous sodium sulfate, and the solvent was evaporated under reduced pressure. The residue was purified by silica gel column chromatography (ethyl acetate/petroleum ether) to give the title compound (14.1 g, containing impurity). This was used for the next step without further purification.

$^1$H NMR (400 MHz, DMSO-d$_6$) δ3.86 (3H, s), 6.63 (1H, t, J=2.4 Hz), 7.71-7.79 (1H, m), 7.81-7.88 (2H, m), 7.97-8.05 (1H, m), 8.67 (1H, d, J=2.8 Hz).

B) 4-(2-fluoro-4-(1H-pyrazol-1-yl)benzyl)-N-((1S,2S)-2-hydroxycyclohexyl)-5-methylpyridine-2-carboxamide The title compound was obtained by a method similar to that in Example 10, Step B, and then Example 1, Steps B-G.

Example 14

4-(4-(1,3-dimethyl-1H-pyrazol-4-yl)benzyl)-N-((1S,2S)-2-hydroxycyclopentyl)-5-methylpyridine-2-carboxamide Dihydrochloride A) methyl 2-chloro-5-methylisonicotinate Methyl bromo-2-chloroisonicotinate (14.0 g), methylboronic acid (5.00 g), palladium acetate (1.25 g), tricyclohexylphosphine (3.12 g) and tripotassium phosphate (41.4 g) were stirred in a mixture of toluene (265 mL) and water (13 mL) under an argon atmosphere at 100° C. overnight. An insoluble material was filtered off and washed with ethyl acetate, and the filtrate and the washing were combined. The solvent was evaporated under reduced pressure. The obtained residue was purified by silica gel column chromatography (ethyl acetate/hexane) to give the title compound (7.41 g).

MS (ESI+): [M+H]$^+$ 185.9.

B) methyl 4-(4-(benzyloxy)benzyl)-5-methylpicolinate

The title compound was obtained by a method similar to that in Example 6, Steps A, B, E, F.

MS (ESI+): [M+H]$^+$ 348.0.

C) methyl 4-(4-hydroxybenzyl)-5-methylpicolinate

To a solution of methyl 4-(4-(benzyloxy)benzyl)-5-methylpicolinate (2.60 g) in THF (100 mL) was added 10% palladium-carbon (0.3 g) and the mixture was stirred under a hydrogen atmosphere at room temperature overnight. An insoluble material was filtered off through celite, and the solvent was evaporated under reduced pressure to give the title compound. This was used for the next step without further purification.

MS (ESI+): [M+H]$^+$ 257.9.

D) methyl 5-methyl-4-(4-(((trifluoromethyl)sulfonyl)oxy)benzyl)picolinate

Methyl 4-(4-hydroxybenzyl)-5-methylpicolinate obtained in the previous step, 1,1,1-trifluoro-N-phenyl-N-(trifluoromethylsulfonyl)methanesulfonamide (5.34 g), DIPEA (2.90 g) and DMAP (91.0 mg) were stirred in THF (100 mL) at room temperature overnight. The solvent was evaporated under reduced pressure, and the obtained residue was purified by silica gel column chromatography (ethyl acetate/hexane) to give the title compound (2.70 g).

MS (ESI+): [M+H]$^+$ 389.9.

E) methyl 4-(4-(1,3-dimethyl-1H-pyrazol-4-yl)benzyl)-5-methylpicolinate

Methyl 5-methyl-4-(4-(((trifluoromethyl)sulfonyl)oxy)benzyl)picolinate (1.00 g), 1,3-dimethylpyrazole-4-boronic acid pinacol ester (0.627 g), tripotassium phosphate (1.10 g) and Pd(Ph$_3$P)$_4$ (297 mg) were stirred in DMF (50 mL) under an argon atmosphere at 90° C. overnight. To the reaction mixture was added water, and the mixture was extracted with ethyl acetate. The obtained organic layer was washed with water, dried over anhydrous magnesium sulfate, and the solvent was evaporated under reduced pressure. The residue was purified by silica gel column chromatography (ethyl acetate/hexane) to give the title compound (0.550 g). MS (ESI+): [M+H]$^+$ 336.0.

F) 4-(4-(1,3-dimethyl-1H-pyrazol-4-yl)benzyl)-N-((1S,2S)-2-hydroxycyclopentyl)-5-methylpyridine-2-carboxamide The title compound was obtained by a method similar to that in Example 6, Steps G, H. This was used for the next step without further purification.

G) 4-(4-(1,3-dimethyl-1H-pyrazol-4-yl)benzyl)-N-((1S,2S)-2-hydroxycyclopentyl)-5-methylpyridine-2-carboxamide Dihydrochloride To a solution of 4-(4-(1,3-dimethyl-1H-pyrazol-4-yl)benzyl)-N-((1S,2S)-2-hydroxycyclopentyl)-5-methylpyridine-2-carboxamide obtained in the previous step in ethyl acetate (5 mL) was added 4 M hydrochloric acid/ethyl acetate solution (2 mL), and ethanol was further added and the solvent was evaporated under reduced pressure. To the residue were added acetonitrile and ethyl acetate, and the obtained solid was collected by filtration to give the title compound (59.0 mg). $^1$H NMR (300 MHz, DMSO-$d_6$) δ 1.37-1.56 (2H, m), 1.57-1.72 (2H, m), 1.77-1.91 (1H, m), 1.91-2.05 (1H, m), 2.28 (3H, s), 2.34 (3H, s), 3.78 (3H, s), 3.91-4.03 (2H, m), 4.08 (2H, s), 7.19 (2H, d, J=7.9 Hz), 7.37 (2H, d, J=7.9 Hz), 7.83 (1H, s), 7.87 (1H, s), 8.44 (1H, s), 8.50 (1H, d, J=7.5 Hz).

Example 19

N-((1S,2S)-2-hydroxycyclohexyl)-4-(4-methoxybenzyl)-5-methylpyridine-2-carboxamide A) methyl 4-(4-methoxybenzyl)-5-methylpicolinate To a solution of methyl 4-chloro-5-methylpicolinate (500 mg) in THF (20 mL) were successively added 0.5 M THF solution (13.5 mL) of 4-methoxybenzylzinc chloride and bis(tri-t-butylphosphine)palladium(0) (138 mg) under an argon atmosphere at 0° C., and the mixture was stirred at room temperature overnight. To the reaction mixture was added saturated aqueous sodium hydrogen carbonate solution, and the mixture was stirred for 1 hr at room temperature and extracted with ethyl acetate. The obtained organic layer was washed with water, dried over anhydrous magnesium sulfate, and the solvent was evaporated under reduced pressure. The residue was purified by silica gel column chromatography (ethyl acetate/hexane) to give the title compound (80 mg).
MS (ESI+): [M+H]$^+$ 271.9.

B) N-((1S,2S)-2-hydroxycyclohexyl)-4-(4-methoxybenzyl)-5-methylpyridine-2-carboxamide The title compound was obtained by a method similar to that in Example 6, Steps G, H.

Example 20

N-(1-(hydroxymethyl)cyclopentyl)-5-methyl-4-(4-(1-methyl-1H-pyrazol-3-yl)benzyl)pyridine-2-carboxamide 5-Methyl-4-(4-(1-methyl-1H-pyrazol-3-yl)benzyl)picolinic acid (24.6 mg), (1-aminocyclopentyl)methanol (11.1 mg), 4-(4,6-dimethoxy[1.3.5]triazin-2-yl)-4-methylmorpholinium chloride hydrate (26.6 mg) and triethylamine (9.6 mg) were stirred in a mixture of THF (0.6 mL) and methanol (0.4 mL) at room temperature for 2 hr. The reaction mixture was purified by HPLC (Actus Triart C18, water/acetonitrile (containing 0.01 M ammonium carbonate)) to give the title compound (13.3 mg).

Example 34

N-((1S,2S)-2-hydroxycyclopentyl)-5-methyl-4-((6-(1H-pyrazol-1-yl)pyridin-3-yl)methyl)pyridine-2-carboxamide A) 6-(1H-pyrazol-1-yl)nicotinaldehyde 6-Chloropyridine-3-carbaldehyde (20.9 g), pyrazole (12.0 g) and potassium carbonate (30.4 g) were stirred in DMF (215 mL) at 100° C. for 24 hr. The solvent was evaporated under reduced pressure, to the obtained residue was added water, and the mixture was extracted with dichloromethane. The obtained organic layer was washed with saturated brine, dried over anhydrous sodium sulfate, and the solvent was evaporated under reduced pressure to give the title compound (22.8 g).
$^1$H NMR (400 MHz, CDCl$_3$) δ6.52 (1H, t, J=2.4 Hz), 7.79 (1H, s), 8.13 (1H, d, J=8.8 Hz), 8.28 (1H, dd, J=8.8, 2.4 Hz), 8.63 (1H, d, J=2.8 Hz), 8.86 (1H, d, J=1.6 Hz), 10.07 (1H, s).

B) (6-(1-methyl-1H-pyrazol-3-yl)pyridin-3-yl)methanol

To a solution of 6-(1H-pyrazol-1-yl)nicotinaldehyde (22.8 g) in methanol (250 mL) was added sodium borohydride (7.51 g) at 0° C., and the mixture was stirred at the same temperature for 1 hr. To the reaction mixture was added water, and the mixture was extracted with ethyl acetate. The obtained organic layer was washed with water, dried over anhydrous magnesium sulfate, and the solvent was evaporated under reduced pressure. The residue was purified by silica gel column chromatography (ethyl acetate/hexane) to give the title compound (13.4 g).
$^1$H NMR (400 MHz, CDCl$_3$) δ2.44 (1H, brs), 4.71 (2H, d, J=7.6 Hz), 6.46 (1H, t, J=2.0 Hz), 7.73 (1H, d, J=1.2 Hz), 7.81 (1H, dd, J=8.0, 2.0 Hz), 7.91 (1H, d, J=8.0 Hz), 8.33 (1H, d, J=2.0 Hz), 8.53 (1H, d, J=2.8 Hz).

C) N-((1S,2S)-2-hydroxycyclopentyl)-5-methyl-4-((6-(1H-pyrazol-1-yl)pyridin-3-yl)methyl)pyridine-2-carboxamide The title compound was obtained by a method similar to that in Example 1, Steps B-G.

Example 37

5-(difluoromethyl)-N-((1S,2S)-2-hydroxycyclopentyl)-4-(4-(1H-pyrazol-1-yl)benzyl)pyridine-2-carboxamide A) methyl 4-chloro-5-(dibromomethyl)picolinate To a solution of methyl 4-chloro-5-(dibromomethyl)picolinate (27.0 g) in carbon tetrachloride (600 mL) were added N-bromosuccinimide (52.0 g) and 2,2'-azobis(isobutyronitrile) (4.79 g), and the mixture was stirred at 90° C. for 24 hr. The reaction mixture was cooled to room temperature and added to water, and the mixture was extracted twice with dichloromethane. The combined organic layer was dried over anhydrous sodium sulfate, and the solvent was evaporated under reduced pressure. The residue was purified by silica gel column chromatography (ethyl acetate/petroleum ether) to give the title compound (26.4 g, containing byproduct).
MS (ESI+): [M+H]$^+$ 343.7.

B) methyl 4-chloro-5-formylpicolinate

To a solution (500 mL) of methyl 4-chloro-5-(dibromomethyl)picolinate (22.7 g, containing byproduct) in ethanol was added dropwise an aqueous solution (50 mL) of silver nitrate (34.0 g) at room temperature, and the mixture was stirred at 50° C. for 16 hr. The reaction mixture was cooled to room temperature, and the insoluble material was filtered off. The solvent was evaporated under reduced pressure. The residue was diluted with dichloromethane, and added to a saturated aqueous sodium hydrogen carbonate solution. The aqueous layer was extracted twice with dichloromethane, and the combined organic layer was dried over anhydrous sodium sulfate. The solvent was evaporated under reduced pressure. The residue was purified by silica gel column chromatography (ethyl acetate/petroleum ether) to give the title compound (4.01 g).
$^1$H NMR (400 MHz, CDCl$_3$) δ4.05 (3H, s), 8.24 (1H, s), 9.12 (1H, s), 10.54 (1H, s).

C) methyl 4-chloro-5-(difluoromethyl)picolinate

To a solution of methyl 4-chloro-5-formylpicolinate (9.95 g) in dichloromethane (120 mL) was added dropwise N,N-diethylaminosulfur trifluoride (20.1 g), and the mixture was stirred at room temperature for 16 hr. The reaction mixture was added to a saturated aqueous sodium hydrogen carbonate solution, and the aqueous layer was extracted twice with dichloromethane. The combined organic layer was dried over anhydrous sodium sulfate, and the solvent was evaporated under reduced pressure. The residue was purified by silica gel column chromatography (ethyl acetate/petroleum ether) to give the title compound (7.76 g).
MS (ESI+): [M+H]$^+$ 221.7.

D) 5-(difluoromethyl)-N-((1S,2S)-2-hydroxycyclopentyl)-4-(4-(1H-pyrazol-1-yl)benzyl)pyridine-2-carboxamide The title compound was obtained by a method similar to that in Example 1, Steps D-G.

Example 43

5-ethyl-N-((1S,2S)-2-hydroxycyclohexyl)-4-(4-(1H-pyrazol-1-yl)benzyl)pyridine-2-carboxamide A) methyl 4-(4-(1H-pyrazol-1-yl)benzyl)-5-ethylpicolinate A mixture of methyl 4-(4-(1H-pyrazol-1-yl)benzyl)-5-vinylpicolinate (208 mg) and 10% palladium-carbon (21.0 mg) in THF (13 mL) was stirred under a hydrogen atmosphere at room temperature for 3 hr. The insoluble material was removed by filtration. The solvent was evaporated under reduced pressure, and the obtained residue was purified by silica gel column chromatography (ethyl acetate/hexane) to give the title compound (184 mg).
MS (ESI+): [M+H]$^+$ 322.0.

B) 5-ethyl-N-((1S,2S)-2-hydroxycyclohexyl)-4-(4-(1H-pyrazol-1-yl)benzyl)pyridine-2-carboxamide The title compound was obtained by a method similar to that in Example 6, Steps G-H.

Example 53

5-chloro-4-(2-fluoro-4-(1H-pyrazol-1-yl)benzyl)-N-((1S,2S)-2-hydroxycyclopentyl)pyridine-2-carboxamide A) 1-(4-chloro-3-fluorophenyl)-1H-pyrazole To a mixture of 4-chloro-3-fluorophenylboronic acid (35.0 g) and pyrazole (20.4 g) in methanol (500 mL) was added copper(I) oxide (28.6 g), and the mixture was stirred under an oxygen atmosphere at room temperature for 16 hr. The resulting solid was filtered off, and the solid was washed 4 times with methanol (200 mL). The combined filtrate was evaporated under reduced pressure, and the residue was purified by silica gel column chromatography (ethyl acetate/petroleum ether) to give the title compound (21.0 g).
$^1$H NMR (400 MHz, CDCl$_3$) δ6.49 (1H, t, J=2.0 Hz), 7.39-7.51 (2H, m), 7.57 (1H, dd, J=10.0, 2.0 Hz), 7.73 (1H, d, J=1.6 Hz), 7.89 (1H, d, J=2.4 Hz).

B) 5-chloro-4-(2-fluoro-4-(1H-pyrazol-1-yl)benzyl)-N-((1S,2S)-2-hydroxycyclopentyl)pyridine-2-carboxamide The title compound was obtained by a method similar to that in Example 6, Steps D-H.

Example 56

1,5-anhydro-2,4-dideoxy-2-(((5-methoxy-4-(4-(1H-pyrazol-1-yl)benzyl)pyridin-2-yl)carbonyl)amino)-L-threo-pentitol A) 2-(hydroxymethyl)-5-methoxy-4H-pyran-4-one To an aqueous solution (50 mL) of 5-hydroxy-2-(hydroxymethyl)-4H-pyran-4-one (11.4 g) and potassium hydroxide (4.95 g) was added dropwise dimethyl sulfate (10.1 g), and the mixture was stirred at room temperature overnight. The obtained solid was collected by filtration to give the title compound (7.50 g).
$^1$H NMR (300 MHz, DMSO-d$_6$) δ3.64 (3H, s), 4.28-4.30 (2H, m), 5.67 (1H, t, J=6.9 Hz), 6.29 (1H, s), 8.08 (1H, s).

B) 5-methoxy-4-oxo-4H-pyran-2-carbaldehyde

To a solution of 2-(hydroxymethyl)-5-methoxy-4H-pyran-4-one (3.70 g) in methanol (150 mL) was added manganese dioxide (10.3 g), and the mixture was heated under reflux for 4 hr. An insoluble material was filtered off through celite, and the solvent was evaporated under reduced pressure to give the title compound. This was used for the next step without further purification.

C) 5-methoxy-4-oxo-4H-pyran-2-carboxylic Acid

To a solution of 5-methoxy-4-oxo-4H-pyran-2-carbaldehyde obtained in the previous step in methanol (100 mL) were added 1 M aqueous sodium hydroxide solution (24 mL) and water (60 mL), silver oxide (5.49 g) was added, and the mixture was stirred at room temperature for 3 hr. An insoluble material was filtered off through celite, and the solvent was evaporated under reduced pressure. The obtained residue was dissolved in water, the mixture was acidified with 1 M hydrochloric acid, and the obtained solid was collected by filtration to give the title compound (3.20 g).
$^1$H NMR (300 MHz, DMSO-d$_6$) δ3.70 (3H, s), 6.91 (1H, s), 8.26 (1H, s) (* peak of one "COOH group" was not observed).

D) 5-methoxy-4-oxo-1,4-dihydropyridine-2-carboxylic Acid

A mixture of 5-methoxy-4-oxo-4H-pyran-2-carboxylic acid (22.2 g) in 28% aqueous ammonia (300 mL) was stirred at room temperature for 16 hr. The solvent was evaporated under reduced pressure, and the obtained residue was acidified with 2 M hydrochloric acid. The precipitate was collected by filtration, washed with water, and dried under reduced pressure to give the title compound (17.4 g).

$^1$H NMR (400 MHz, DMSO-d$_6$) δ3.84 (3H, s), 7.24 (1H, s), 7.88 (1H, s (* peaks of one "COOH group" and one "NH group" were not observed)).

E) methyl 4-chloro-5-methoxypicolinate

To 5-methoxy-4-oxo-1,4-dihydropyridine-2-carboxylic acid (7.94 g) was added phosphorus oxychloride (60 mL), and the mixture was stirred under a nitrogen atmosphere at 90° C. for 3 hr. The solvent was evaporated under reduced pressure, methanol (60 mL) and DIPEA (12.1 g) were added to the obtained residue at 0° C., and the mixture was further stirred at room temperature for 2 hr. The solvent was evaporated under reduced pressure, and the residue was purified by silica gel column chromatography (ethyl acetate/petroleum ether) to give the title compound (9.00 g).

$^1$H NMR (400 MHz, CDCl$_3$) δ3.99 (3H, s), 4.08 (3H, s), 8.17 (1H, s), 8.36 (1H, s).

F) 1,5-anhydro-2,4-dideoxy-2-(((5-methoxy-4-(4-(1H-pyrazol-1-yl)benzyl)pyridin-2-yl)carbonyl)amino)-L-threo-pentitol The title compound was obtained by a method similar to that in Example 1, Steps D-G.

Example 57

4-((6-chloropyridin-3-yl)methyl)-N-(2-trans-hydroxycyclohexyl)-5-methoxypyridine-2-carboxamide A) 4-bromo-N-(2-trans-hydroxycyclohexyl)-5-methoxypicolinamide To a solution of 5-methoxy-4-oxo-1,4-dihydropyridine-2-carboxylic acid (3.00 g) in DMF (30 mL) was added phosphorus tribromide (9.75 g) at 0° C., and the mixture was stirred at room temperature for 16 hr. To the reaction mixture was added DIPEA (14.7 g) at 0° C., and the mixture was stirred at room temperature for 0.5 hr. Furthermore, a mixture of trans-2-aminocyclohexanol hydrochloride (4.30 g), HOBt (3.10 g), WSC (6.84 g) and DIPEA (9.18 g) in DMF (50 mL) was added and the mixture was stirred under a nitrogen atmosphere at room temperature for 16 hr. The reaction mixture was added to water, and the aqueous layer was extracted 4 times with ethyl acetate. The combined organic layer was washed with saturated brine, dried over anhydrous sodium sulfate, and the solvent was evaporated under reduced pressure. The residue was washed with tert-butyl methyl ether to give the title compound (348 mg).

MS (ESI+): [M+H]$^+$ 328.9.

B) 4-((6-chloropyridin-3-yl)methyl)-N-(2-trans-hydroxycyclohexyl)-5-methoxypyridine-2-carboxamide The title compound was obtained by a method similar to that in Example 19, Step A.

Example 58

N-(trans-2-hydroxycyclohexyl)-5-methoxy-4-((6-(1-methyl-1H-pyrazol-4-yl)pyridin-3-yl)methyl)pyridine-2-carboxamide 4-((6-Chloropyridin-3-yl)methyl)-N-(2-trans-hydroxycyclohexyl)-5-methoxypyridine-2-carboxamide (100 mg), 1-methylpyrazole-4-boronic acid pinacol ester (66.4 mg), potassium carbonate (110 mg) and Pd(Ph$_3$P)$_4$ (30.7 mg) were stirred in a mixture of 1,4-dioxane (5 mL) and water (1 mL) under a nitrogen atmosphere at 80° C. for 16 hr. The solvent was evaporated under reduced pressure, and the residue was separated by adding water and ethyl acetate. The aqueous layer was extracted 3 times with ethyl acetate. The solvent of the combined organic layer was evaporated under reduced pressure. The residue was purified by HPLC (Fuji C18, water/acetonitrile (containing 0.1% ammonium chloride/TFA)) and the eluate was evaporated under reduced pressure, and the residue was freeze-dried to give the title compound (25.0 mg).

$^1$H NMR (400 MHz, DMSO-d$_6$) δ 1.15-1.30 (4H, m), 1.55-1.64 (2H, m), 1.80-1.95 (2H, m), 3.35-3.45 (1H, m), 3.48-3.61 (1H, m), 3.87 (3H, s), 3.95-4.07 (5H, m), 4.67 (1H, d, J=5.6 Hz), 7.53-7.64 (2H, m), 7.82 (1H, s), 7.93 (1H, s), 8.20 (1H, d, J=7.6 Hz), 8.22 (1H, s), 8.31 (1H, s), 8.41 (1H, s).

Example 64

N-((1S,2S)-2-hydroxycyclohexyl)-5-methoxy-4-(4-(1-methyl-1H-pyrazol-4-yl)benzyl)pyridine-2-carboxamide 4-(4-Bromobenzyl)-N-((1S,2S)-2-hydroxycyclohexyl)-5-methoxypyridine-2-carboxamide (530 mg), 1-methylpyrazole-4-boronic acid pinacol ester (315 mg), potassium carbonate (522 mg) and Pd(Ph$_3$P)$_4$ (146 mg) were stirred in a mixture of 1,4-dioxane (25 mL) and water (5 mL) under a nitrogen atmosphere at 80° C. for 16 hr. The solvent of the reaction mixture was evaporated under reduced pressure, and the residue was purified by silica gel column chromatography (ethyl acetate/petroleum ether) and washed with a tert-butyl methyl ether-dichloromethane mixture to give the title compound (245 mg).

$^1$H NMR (400 MHz, DMSO-d$_6$) δ 1.20-1.36 (4H, m), 1.56-1.70 (2H, m), 1.85-1.98 (2H, m), 3.38-3.49 (1H, m), 3.50-3.63 (1H, m), 3.94-4.09 (5H, m), 4.65 (1H, d, J=5.2 Hz), 7.19 (2H, d, J=8.4 Hz), 7.49 (2H, d, J=8.0 Hz), 7.80 (1H, s), 8.16 (1H, d, J=8.0 Hz), 8.31 (1H, s).

Example 65

5-chloro-N-((1S,2S)-2-hydroxycyclohexyl)-6-methyl-4-(4-(1-methyl-1H-pyrazol-3-yl)benzyl)pyridine-2-carboxamide A) methyl 5-chloro-6-methylpicolinate The title compound was obtained by a method similar to that in Example 6, Step F.

MS (ESI+): [M+H]$^+$ 185.9.

B) methyl 5-chloro-6-methyl-4-(4-(1-methyl-1H-pyrazol-3-yl)benzyl)picolinate

Methyl 5-chloro-6-methylpicolinate (371 mg), 4,4,4',4',5,5,5',5'-octamethyl-2,2'-bi-1,3,2-dioxaborolane (508 mg), di-mu-methoxobis(1,5-cyclooctadiene)diiridium(I) (39.8 mg) and 4,4'-di-tert-butyl-2,2'-bipyridine (16.1 mg) were stirred in tert-butyl methyl ether (4 mL) under microwave radiation at 80° C. for 0.5 hr. To the reaction mixture were further added 3-(4-(chloromethyl)phenyl)-1-methyl-1H-pyrazole hydrochloride (486 mg), potassium hydroxide (337 mg), water (1 mL) and Pd(dppf)Cl$_2$ DCM (82.0 mg), and the mixture was stirred under microwave radiation at 80° C. for 15 min. An insoluble material was removed by filtration, and washed with water and ethyl acetate. The filtrate was partitioned, and the organic layer was extracted with ethyl acetate. The combined organic layer was washed with saturated brine, dried over anhydrous magnesium sulfate, and the solvent was evaporated under reduced pressure. The residue was purified by silica gel column chromatography (ethyl acetate/hexane) to give the title compound (157 mg).
MS (ESI+): [M+H]$^+$ 356.0.

C) 5-chloro-N-((1S,2S)-2-hydroxycyclohexyl)-6-methyl-4-(4-(1-methyl-1H-pyrazol-3-yl)benzyl)pyridine-2-carboxamide The title compound was obtained by a method similar to that in Example 1, Steps F and G.

Example 67

5-cyano-N-((1S,2S)-2-hydroxycyclohexyl)-4-(4-(1H-pyrazol-1-yl)benzyl)pyridine-2-carboxamide A) methyl 2-chloro-5-cyanoisonicotinate Methyl 5-bromo-2-chloroisonicotinate (15.0 g) and copper(I) cyanide (5.36 g) were stirred in DMA (200 mL) under a nitrogen atmosphere at 170° C. for 5 hr. The reaction mixture was cooled to room temperature, saturated aqueous ammonium chloride solution was added, and the mixture was extracted with ethyl acetate. The obtained organic layer was washed with saturated brine, dried over anhydrous magnesium sulfate, and the solvent was evaporated under reduced pressure. The residue was purified by silica gel column chromatography (ethyl acetate/hexane) to give the title compound (4.50 g).
$^1$H NMR (300 MHz, CDCl$_3$) δ4.06 (3H, s), 8.02 (1H, s), 8.84 (1H, s).

B) 6-chloro-4-(hydroxymethyl)nicotinonitrile

To a solution of methyl 2-chloro-5-cyanoisonicotinate (3.43 g) in methanol (218 mL) was added sodium borohydride (2.78 g) at 0° C., and the mixture was stirred at room temperature for 2 hr. To the reaction mixture was added water, and the mixture was extracted twice with ethyl acetate. The combined organic layer was washed with saturated brine, dried over anhydrous sodium sulfate, and the solvent was evaporated under reduced pressure. The residue was purified by silica gel column chromatography (ethyl acetate/hexane) to give the title compound (907 mg).
MS (ESI+): [M+H]$^+$ 168.9.

C) methyl 4-(4-(1H-pyrazol-1-yl)benzyl)-5-cyanopicolinate

To a solution of 6-chloro-4-(hydroxymethyl)nicotinonitrile (865 mg) in acetonitrile (51 mL) was added dropwise phosphorus tribromide (1.70 g) at 0° C., and the mixture was stirred at room temperature for 4 hr. To the reaction mixture was added saturated aqueous sodium hydrogen carbonate solution under ice-cooling, and the mixture was extracted twice with ethyl acetate. The combined organic layer was washed with water and saturated brine, dried over anhydrous sodium sulfate, and the solvent was evaporated under reduced pressure. The residue was purified twice by silica gel column chromatography (ethyl acetate/hexane) to give a solid (1.09 g). To a solution of the obtained solid and 1-(4-(4,4,5,5-tetramethyl-1,3,2-dioxaborolan-2-yl)phenyl)-1H-pyrazole (1.15 g) in DME (36 mL) were added Pd(Ph$_3$P)$_4$ (495 mg) and 2 M aqueous sodium carbonate solution (17 mL), and the mixture was stirred under a nitrogen atmosphere at 100° C. overnight. To the reaction mixture was added water, and the mixture was extracted twice with ethyl acetate. The combined organic layer was washed with saturated brine, dried over anhydrous sodium sulfate, and the solvent was evaporated under reduced pressure. The residue was purified by silica gel column chromatography (ethyl acetate/hexane) to give a solid (123 mg). The obtained resultant product, Pd(dppf)Cl$_2$ DCM (339 mg) and triethylamine (41.6 mg) were stirred in a mixture of methanol (3 mL) and DMF (5 mL) in the presence of carbon monoxide (3 atm) at 80° C. for 5 hr. The solvent was evaporated under reduced pressure, to the obtained residue were added ethyl acetate and water, and an insoluble material was removed by filtration. The aqueous layer was extracted twice with ethyl acetate. The combined organic layer was washed with water and saturated brine, dried over anhydrous sodium sulfate, and the solvent was evaporated under reduced pressure. The obtained residue was purified by silica gel column chromatography (ethyl acetate/hexane) to give the title compound (44.5 mg).
MS (ESI+): [M+H]$^+$ 318.9.

D) 4-(4-(1H-pyrazol-1-yl)benzyl)-5-cyanopicolinic Acid

A mixed solution of methyl 4-(4-(1H-pyrazol-1-yl)benzyl)-5-cyanopicolinate (41.4 mg), 2 M aqueous hydroxide solution (0.26 mL) in THF (3 mL) and methanol (3 mL) was stirred at 60° C. for 1 hr. After cooling, to the reaction mixture was added 2 M hydrochloric acid (0.52 mL) at 0° C., and the solvent was evaporated under reduced pressure to give the title compound. This was used for the next step without further purification.
MS (ESI+): [M+H]$^+$ 304.9.

E) 5-cyano-N-((1S,2S)-2-hydroxycyclohexyl)-4-(4-(1H-pyrazol-1-yl)benzyl)pyridine-2-carboxamide To a mixture of 4-(4-(1H-pyrazol-1-yl)benzyl)-5-cyanopicolinic acid obtained in the previous step, (1S,2S)-2-aminocyclohexanol hydrochloride (23.9 mg), WSC (33.1 mg), HOBt monohydrate (26.7 mg) in DMF (2.1 mL) was added triethylamine (53.2 mg), and the mixture was stirred at room temperature overnight. The reaction mixture was diluted with water, and extracted twice with ethyl acetate. The combined organic layer was washed successively with saturated aqueous sodium hydrogen carbonate solution, water and saturated brine, dried over anhydrous sodium sulfate, and the solvent was evaporated under reduced pressure. The residue was purified by silica gel column chromatography (ethyl acetate/hexane) to give the title compound (30.4 mg).
$^1$H NMR (300 MHz, CDCl$_3$) δ1.29-1.49 (4H, m), 1.72-1.84 (2H, m), 2.06-2.15 (2H, m), 3.02 (1H, brs), 3.48 (1H, brs), 3.74-3.89 (1H, m), 4.27 (2H, s), 6.42-6.51 (1H, m), 7.30-7.39 (2H, m), 7.61-7.76 (3H, m), 7.90 (1H, d, J=2.4 Hz), 7.97 (1H, d, J=7.5 Hz), 8.17 (1H, s), 8.75 (1H, s).

Example 68

N-((1S,2S)-2-hydroxycyclopentyl)-6-methoxy-4-(4-(1H-pyrazol-1-yl)benzyl)pyridine-2-carboxamide A) methyl 2-chloro-6-methoxyisonicotinate To a solution of methyl 2,6-dichloroisonicotinate (2.90 g) in methanol (30 mL) was added a 28% methanol solution (3.7 mL) of sodium methoxide, and the mixture was refluxed under heating for 1 hr. To the reaction mixture was added 0.5 M hydrochloric acid (30 mL), and the obtained solid was collected by filtration to give the title compound (245 mg).
$^1$H NMR (400 MHz, CDCl$_3$) δ3.94 (3H, s), 3.98 (3H, s), 7.22 (1H, s), 7.43 (1H, s).

B) N-((1S,2S)-2-hydroxycyclopentyl)-6-methoxy-4-(4-(1H-pyrazol-1-yl)benzyl)pyridine-2-carboxamide The title compound was obtained by a method similar to that in Example 6, Steps A-H.

Example 72

N-((1S,2S)-2-hydroxycyclopentyl)-5,6-dimethyl-4-(4-(1-methyl-1H-pyrazol-3-yl)benzyl)pyridine-2-carboxamide A) 3-(2-methyl-1,3-dioxolan-2-yl)butan-2-one 1,1-Diacetylethane (50.7 g), ethylene glycol (27.6 g) and p-toluenesulfonic acid monohydrate (0.845 g) were heated under reflux in benzene (500 mL) while evaporating water by using a Dean-Stark apparatus for 3 hr. To the reaction mixture was added 10% sodium hydroxide-saturated brine solution (200 mL), and the organic layer was separated, dried over anhydrous sodium sulfate, and the solvent was evaporated under reduced pressure. The residue was distilled under reduced pressure (20 torr) to give the title compound (34.9 g).
$^1$H NMR (400 MHz, CDCl$_3$) δ1.11 (3H, d, J=6.8 Hz), 1.25 (3H, s), 2.20 (3H, s), 2.88 (1H, q, J=7.2 Hz), 3.85-4.00 (4H, m).

B) 5,6-dimethyl-4-oxo-4H-pyran-2-carboxylic Acid 3-(2-Methyl-1,3-dioxolan-2-yl)butan-2-one (34.9 g) and sodium methoxide (11.9 g) were stirred in methanol (175 mL) at 15° C. for 2 hr, diethyl oxalate (32.2 g) was added, and the mixture was stirred at 15° C. for 2 days, and further at 30° C. for 1 day. To the reaction mixture was added 5% aqueous sulfuric acid solution (120 mL) and the solvent was evaporated under reduced pressure. The obtained residue was diluted with water, and extracted twice with dichloromethane. The organic layer was dried over anhydrous sodium sulfate, and the solvent was evaporated under reduced pressure. To the obtained residue (63.5 g) was added 0.5 M hydrochloric acid (290 mL), and the mixture was stirred at 10° C. for 16 hr, and further heated under reflux for 2 hr. The reaction mixture was cooled to 0° C., and the obtained solid was collected by filtration to give the title compound (20.0 g).

$^1$H NMR (400 MHz, DMSO-d$_6$) δ1.84 (3H, s), 2.34 (3H, s), 6.76 (1H, s).
(* The peak of one "COOH group" was not observed.)

C) 5,6-dimethyl-4-oxo-1,4-dihydropyridine-2-carboxylic Acid

To 5,6-dimethyl-4-oxo-4H-pyran-2-carboxylic acid (10.0 g) was added 28% aqueous ammonia (50 mL), and the mixture was stirred in a sealed tube at 100° C. for 16 hr. A similar reaction in the same scale was performed again. The combined reaction mixture was concentrated under reduced pressure, water and hydrochloric acid were added to the obtained residue to adjust the pH to 3, and the obtained solid was collected by filtration to give the title compound (19.8 g).
$^1$H NMR (400 MHz, CD$_3$OD) δ2.23 (3H, s), 2.65 (3H, s), 7.49 (1H, s).

D) methyl 4-chloro-5,6-dimethylpicolinate

A mixture of 5,6-dimethyl-4-oxo-1,4-dihydropyridine-2-carboxylic acid (6.00 g) and phosphorus oxychloride (60 mL) was stirred under a nitrogen atmosphere at 90° C. for 9 hr. The solvent is almost entirely evaporated under reduced pressure, methanol (60 mL) and DIPEA (18.5 g) were added to the obtained residue at 0° C., and the reaction mixture was stirred at room temperature for 2 hr. The solvent was evaporated under reduced pressure, and the residue was purified by silica gel column chromatography (ethyl acetate/petroleum ether) to give the title compound (5.30 g).
$^1$H NMR (400 MHz, CDCl$_3$) δ2.42 (3H, s), 2.65 (3H, s), 3.99 (3H, s), 7.98 (1H, s).

E) methyl 5,6-dimethyl-4-(4,4,5,5-tetramethyl-1,3,2-dioxaborolan-2-yl)picolinate Methyl 4-chloro-5,6-dimethylpicolinate (887 mg), bis(pinacolato)diboron (2.26 g), Pd$_2$(dba)$_3$ (408 mg), X-phos (421 mg) and potassium acetate (870 mg) were stirred in 1,4-dioxane (20 mL) under a nitrogen atmosphere at 65° C. for 16 hr. The solvent was evaporated under reduced pressure, and the obtained residue was purified by silica gel column chromatography (dichloromethane/methanol) to give the title compound (1.60 g, containing bis(pinacolato)diboron).
$^1$H NMR (400 MHz, CDCl$_3$) δ1.35 (12H, s), 2.51 (3H, s), 2.59 (3H, s), 3.96 (3H, s), 8.24 (1H, s).

F) methyl 5,6-dimethyl-4-(4-(1-methyl-1H-pyrazol-3-yl)benzyl)picolinate

Methyl 5,6-dimethyl-4-(4,4,5,5-tetramethyl-1,3,2-dioxaborolan-2-yl)picolinate (325 mg, containing bis(pinacolato)diboron), 3-(4-(chloromethyl)phenyl)-1-methyl-1H-pyrazole hydrochloride (271 mg), potassium carbonate (525 mg) and Pd(dppf)Cl$_2$ DCM (91.0 mg) were stirred in a mixture of DME (8 mL) and water (0.5 mL) under a nitrogen atmosphere at room temperature overnight. The reaction mixture was diluted with ethyl acetate, dried over sodium sulfate, and the solvent was evaporated under reduced pressure. The obtained residue was purified by silica gel column chromatography (ethyl acetate/methanol) to give the title compound (111 mg). The resultant product was used for the next step without further purification.
MS (ESI+): [M+H]$^+$ 336.0.

G) 5,6-dimethyl-4-(4-(1-methyl-1H-pyrazol-3-yl)benzyl)picolinic Acid

To a mixed solution of methyl 5,6-dimethyl-4-(4-(1-methyl-1H-pyrazol-3-yl)benzyl)picolinate (111 mg) in ethanol (4 mL) and THF (4 mL) was added 1 M aqueous sodium hydroxide solution (2.0 mL) at 0° C., and the mixture was stirred at room temperature overnight. The reaction mixture was neutralized with 1 M hydrochloric acid (2 mL) at 0° C. The solvent was evaporated under reduced pressure, and the residue was extracted 3 times with ethyl acetate. The obtained organic layer was washed with saturated brine, dried over anhydrous sodium sulfate, and the solvent was evaporated under reduced pressure to give the title compound (96.0 mg).

MS (ESI+): [M+H]$^+$ 322.0.

H) N-((1S,2S)-2-hydroxycyclopentyl)-5,6-dimethyl-4-(4-(1-methyl-1H-pyrazol-3-yl)benzyl)pyridine-2-carboxamide A mixture of 5,6-dimethyl-4-(4-(1-methyl-1H-pyrazol-3-yl)benzyl)picolinic acid (30.0 mg), (1S,2S)-2-aminocyclopentanol hydrochloride (19.3 mg), WSC (26.8 mg), HOBt (18.9 mg) and triethylamine (28.3 mg) in DMF (1 mL) was stirred at room temperature overnight. To the reaction mixture was added saturated aqueous sodium hydrogen carbonate solution and extracted twice with ethyl acetate. The obtained organic layer was washed with saturated brine, dried over anhydrous sodium sulfate, and the solvent was evaporated under reduced pressure. The residue was purified by silica gel column chromatography (ethyl acetate/methanol), and solidified with ethyl acetate-hexane to give the title compound (30.0 mg).

$^1$H NMR (300 MHz, CDCl$_3$) δ1.60-1.96 (4H, m), 2.03-2.18 (1H, m), 2.22 (3H, s), 2.24-2.34 (1H, m), 2.53 (3H, s), 3.94 (3H, s), 3.95-4.03 (1H, m), 4.05 (2H, s), 4.08-4.18 (1H, m), 4.71 (1H, brs), 6.49 (1H, d, J=1.7 Hz), 7.11 (2H, d, J=8.0 Hz), 7.36 (1H, d, J=1.9 Hz), 7.69 (2H, d, J=8.0 Hz), 7.88 (1H, s), 8.20 (1H, brs).

Example 73

4-((6-chloropyridin-3-yl)methyl)-N-((1S,2S)-2-hydroxycyclohexyl)-5,6-dimethylpyridine-2-carboxamide

A) 4-bromo-N-((1S,2S)-2-hydroxycyclohexyl)-5,6-dimethylpicolinamide

To a solution of 5,6-dimethyl-4-oxo-1,4-dihydropyridine-2-carboxylic acid (2.01 g) in DMF (20 mL) was added phosphorus tribromide (6.50 g) at 0° C., and the mixture was stirred at room temperature for 16 hr. To the reaction mixture was added DIPEA (6.50 g) at 0° C. to adjust the reaction solution to pH=7-8. To the reaction mixture were added (1S,2S)-2-aminocyclohexanol hydrochloride (2.92 g), HOBt (1.62 g), WSC (4.61 g) and DIPEA (4.64 g) and the mixture was stirred under a nitrogen atmosphere at room temperature for 16 hr. Three batches of the above reaction were performed and mixed at this time point. The reaction mixture was poured into water, and the mixture was extracted 8 times with ethyl acetate. The combined organic layer was dried over anhydrous sodium sulfate and the solvent was evaporated under reduced pressure. The residue was purified twice by silica gel column chromatography (ethyl acetate/dichloromethane) to give the title compound (1.80 g).

$^1$H NMR (400 MHz, CDCl$_3$) δ1.25-1.45 (4H, m), 1.75-1.86 (2H, m), 2.05-2.19 (2H, m), 2.43 (3H, s), 2.58 (3H, s), 3.41-3.51 (1H, m), 3.51-3.63 (1H, m), 3.78-3.89 (1H, m), 7.98 (1H, d, J=7.6 Hz), 8.19 (1H, s).

B) 4-((6-chloropyridin-3-yl)methyl)-N-((1S,2S)-2-hydroxycyclohexyl)-5,6-dimethylpyridine-2-carboxamide A solution of 4-bromo-N-((1S,2S)-2-hydroxycyclohexyl)-5,6-dimethylpicolinamide (620 mg), 0.5 M THF solution (3.8 mL) of (2-chloro-5-pyridyl)methylzinc chloride, bis(tri-t-butylphosphine)palladium(0) (97.0 mg) in THF (15 mL) was heated under reflux under a nitrogen atmosphere for 16 hr. The solvent was evaporated under reduced pressure, and the residue was purified by silica gel column chromatography (dichloromethane/methanol). A similar reaction and purification was performed using 4-bromo-N-((1S,2S)-2-hydroxycyclohexyl)-5,6-dimethylpicolinamide (980 mg), and the combined crude product was purified by HPLC (Fuji C18, water/acetonitrile (containing 0.1% ammonium chloride/TFA)) to give the title compound (300 mg).

$^1$H NMR (400 MHz, CDCl$_3$) δ 1.26-1.49 (4H, m), 1.72-1.83 (2H, m), 2.01-2.18 (2H, m), 2.21 (3H, s), 2.55 (3H, s), 3.47-3.58 (2H, m), 3.76-3.90 (1H, m), 4.02 (2H, s), 7.24 (1H, d, J=8.4 Hz), 7.33 (1H, dd, J=8.0, 2.0 Hz), 7.85 (1H, s), 8.11 (1H, d, J=6.8 Hz), 8.22 (1H, s).

Example 74

N-((1S,2S)-2-hydroxycyclohexyl)-5,6-dimethyl-4-((6-(1-methyl-1H-pyrazol-3-yl)pyridin-3-yl)methyl)pyridine-2-carboxamide 4-((6-Chloropyridin-3-yl)methyl)-N-((1S,2S)-2-hydroxycyclohexyl)-5,6-dimethylpyridine-2-carboxamide (100 mg), 1-methyl-3-(4,4,5,5-tetramethyl-1,3,2-dioxaborolan-2-yl)-1H-pyrazole (111 mg), potassium carbonate (148 mg) and Pd(Ph$_3$P)$_4$ (30.9 mg) were stirred in a mixture of THF (5 mL) and water (0.5 mL) under an argon atmosphere at 80° C. overnight. To the reaction mixture was added water, and the mixture was extracted with ethyl acetate. The obtained organic layer was washed with saturated brine, dried over anhydrous sodium sulfate, and the solvent was evaporated under reduced pressure. The residue was purified by silica gel column chromatography (ethyl acetate/methanol) to give the title compound (84.0 mg).

$^1$H NMR (300 MHz, CDCl$_3$) δ1.24-1.52 (4H, m), 1.78 (2H, d, J=9.5 Hz), 2.02-2.17 (2H, m), 2.20 (3H, s), 2.53 (3H, s), 3.43-3.58 (1H, m), 3.65 (1H, d, J=3.8 Hz), 3.72-3.88 (1H, m), 3.96 (3H, s), 4.05 (2H, s), 6.81 (1H, d, J=2.2 Hz), 7.34-7.42 (2H, m), 7.79 (1H, d, J=8.2 Hz), 7.90 (1H, s), 8.11 (1H, d, J=7.6 Hz), 8.44 (1H, s).

Example 84

N-((1S,2S)-2-hydroxycyclohexyl)-5,6-dimethyl-4-((6-methylpyridin-3-yl)methyl)pyridine-2-carboxamide 4-((6-Chloropyridin-3-yl)methyl)-N-((1S,2S)-2-hydroxycyclohexyl)-5,6-dimethylpyridine-2-carboxamide (150 mg), trimethylboroxine (101 mg), cesium carbonate (196 mg) and Pd(Ph$_3$P)$_4$ (65.5 mg) were stirred in DME (10 mL) under an argon atmosphere at 90° C. overnight. To the reaction mixture was added water, and the mixture was extracted with ethyl acetate. The obtained organic layer was washed with water, dried over anhydrous magnesium sulfate, and the solvent was evaporated under reduced pressure. The residue was purified by silica gel column chromatography (ethyl acetate/methanol) to give the title compound.

¹H NMR (300 MHz, CDCl₃) δ 1.13-1.56 (4H, m), 1.71-1.86 (2H, m), 2.01-2.16 (2H, m), 2.21 (2H, s), 2.51 (2H, s), 2.53 (2H, s), 3.44-3.61 (1H, m), 3.72-3.88 (1H, m), 3.99 (2H, s), 7.05 (1H, d, J=7.9 Hz), 7.20-7.25 (1H, m), 7.83 (1H, s), 8.10 (1H, d, J=6.6 Hz), 8.32 (1H, s).

Example 87

1,5-anhydro-2,4-dideoxy-2-(((6-methoxy-5-methyl-4-(4-(1-methyl-1H-pyrazol-3-yl)benzyl)pyridin-2-yl)carbonyl)amino)-L-threo-pentitol A) 6-chloro-3,4-diiodo-2-methoxypyridine To a solution of diisopropylamine (6.07 g) in THF (150 mL) was added dropwise 1.6 M hexane solution (34.4 mL) of n-butyllithium at −78° C., and the mixture was stirred at the same temperature for 1 hr. At the same temperature, a solution of 2-chloro-6-methoxypyridine (7.18 g) in THF (20 mL) was added dropwise, the mixture was stirred at −50° C. for 2 hr, and a solution of iodine (13.3 g) in THF (50 mL) was added dropwise. The temperature was raised to room temperature and the mixture was stirred overnight. To the reaction mixture was added saturated aqueous sodium thiosulfate solution and the solvent was evaporated under reduced pressure. The residue was extracted with ethyl acetate, the organic layer was washed with saturated brine, dried over anhydrous magnesium sulfate, and the solvent was evaporated under reduced pressure. The residue was purified by silica gel column chromatography (ethyl acetate/hexane) to give the title compound (2.86 g).
MS (ESI+): [M+H]⁺ 396.5.

B) 6-chloro-4-iodo-2-methoxy-3-methylpyridine

To a solution of 6-chloro-3,4-diiodo-2-methoxypyridine (2.46 g) in THF (30 mL) was added dropwise 1.6 M hexane solution (4.1 mL) of n-butyllithium at −78° C., the mixture was stirred for 2 hr and methyl iodide (4.42 g) was added dropwise at the same temperature. The temperature was raised to room temperature and the mixture was stirred overnight. To the reaction mixture was added saturated aqueous sodium thiosulfate solution, and the mixture was extracted twice with ethyl acetate. The organic layer was washed with saturated brine, dried over anhydrous magnesium sulfate, and the solvent was evaporated under reduced pressure. The residue was purified by silica gel column chromatography (ethyl acetate/hexane) to give the title compound (1.04 g).
MS (ESI+): [M+H]⁺ 283.8.

C) 6-chloro-2-methoxy-3-methyl-4-(4,4,5,5-tetramethyl-1,3,2-dioxaborolan-2-yl)pyridine The title compound was obtained by a method similar to that in Example 6, Step D.
MS (ESI+): [M+H]⁺ 283.9.

D) 6-chloro-2-methoxy-3-methyl-4-(4-(1-methyl-1H-pyrazol-3-yl)benzyl)pyridine

The title compound was obtained by a method similar to that in Example 1, Step E.
MS (ESI+): [M+H]⁺ 328.0.

E) 1,5-anhydro-2,4-dideoxy-2-(((6-methoxy-5-methyl-4-(4-(1-methyl-1H-pyrazol-3-yl)benzyl)pyridin-2-yl)carbonyl)amino)-L-threo-pentitol To a mixture of 6-chloro-2-methoxy-3-methyl-4-(4-(1-methyl-1H-pyrazol-3-yl)benzyl)pyridine (229 mg), (3S,4S)-3-aminotetrahydro-2H-pyran-4-ol (123 mg), molybdenum hexacarbonyl (554 mg), trans-di(mu-acetato)bis[o-(di-o-tolylphosphino)benzyl]dipalladium(II) (132 mg), tri(tert-butylphosphonium) tetrafluoroborate (40.6 mg) in THF (1.4 mL) was added DBU (1066 mg) at room temperature, and the mixture was stirred under microwave radiation at 150° C. for 1 hr. To the reaction mixture was added water, and the mixture was extracted twice with ethyl acetate. The combined organic layer was washed with saturated brine, dried over anhydrous magnesium sulfate, and the solvent was evaporated under reduced pressure. The residue was purified by silica gel column chromatography (ethyl acetate/hexane) and NH silica gel column chromatography (ethyl acetate/hexane), and solidified with ethyl acetate-hexane to give the title compound (64.0 mg).

Example 94

5-(difluoromethoxy)-N-((1S,2S)-2-hydroxycyclohexyl)-4-(4-(1H-pyrazol-1-yl)benzyl)pyridine-2-carboxamide A) 4-(4-(1H-pyrazol-1-yl)benzyl)-2-chloro-5-(methoxymethoxy)pyridine The title compound was obtained by a method similar to that in Example 1, Steps D-E.
MS (ESI+): [M+H]⁺ 329.9.

B) 4-(4-(1H-pyrazol-1-yl)benzyl)-6-chloropyridin-3-ol

To a solution of 4-(4-(1H-pyrazol-1-yl)benzyl)-2-chloro-5-(methoxymethoxy)pyridine (247 mg) in THF (9.5 mL) was added 6 M aqueous hydrochloric acid solution (2.4 mL), and the mixture was stirred at 60° C. for 3 hr. To the reaction mixture was added saturated brine, and the mixture was extracted with a mixed solution of ethyl acetate and THF. The obtained organic layer was washed with saturated brine, dried over anhydrous sodium sulfate, and the solvent was evaporated under reduced pressure to give the title compound (294 mg).
MS (ESI+): [M+H]⁺ 285.9.

C) 4-(4-(1H-pyrazol-1-yl)benzyl)-2-chloro-5-(difluoromethoxy)pyridine 4-(4-(1H-pyrazol-1-yl)benzyl)-6-chloropyridin-3-ol (273 mg), sodium chlorodifluoroacetate (426 mg) and potassium carbonate (383 mg) were stirred in a mixture of DMF (12 mL) and water (2.5 mL) under a nitrogen atmosphere at 100° C. overnight. To the reaction mixture was added water, and the mixture was extracted twice with ethyl acetate. The combined organic layer was washed with saturated brine, dried over anhydrous sodium sulfate, and the solvent was evaporated under reduced pressure. The obtained residue was purified by silica gel column chromatography (ethyl acetate/hexane) to give the title compound (125 mg).
MS (ESI+): [M+H]⁺ 335.9.

D) 5-(difluoromethoxy)-N-((1S,2S)-2-hydroxycyclohexyl)-4-(4-(1H-pyrazol-1-yl)benzyl)pyridine-2-carboxamide The title compound was obtained by a method similar to that in Example 87, Step E.

Example 96

1,5-anhydro-2-(((5-chloro-6-methyl-4-(4-(1-methyl-1H-pyrazol-3-yl)benzyl)pyridin-2-yl)carbonyl)amino)-2,4-dideoxy-L-threo-pentitol

A) methyl 5-chloro-6-methylpicolinate

6-Bromo-3-chloro-2-methylpyridine (1.07 g), Pd(dppf)Cl$_2$ DCM (423 mg) and triethylamine (524 mg) were stirred in a mixed solution of methanol (7.5 mL) and DMF (7.5 mL) in the presence of carbon monoxide (3 atm) at 90° C. for 3 hr. The solvent of the reaction mixture was evaporated under reduced pressure, and the obtained residue was purified by silica gel column chromatography (ethyl acetate/hexane) to give the title compound (724 mg).
MS (ESI+): [M+H]$^+$ 185.9.

B) methyl 5-chloro-6-methyl-4-(4-(1-methyl-1H-pyrazol-3-yl)benzyl)picolinate Methyl 5-chloro-6-methylpicolinate (371 mg), 4,4,4',4',5,5,5',5'-octamethyl-2,2'-bi-1,3,2-dioxaborolane (508 mg), di-mu-methoxobis(1,5-cyclooctadiene)diiridium(I) (39.8 mg) and 4,4'-di-tert-butyl-2,2'-bipyridine (16.1 mg) were stirred in tert-butyl methyl ether (4 ml) under microwave radiation at 80° C. for 30 min. To the reaction mixture were added 3-(4-(chloromethyl)phenyl)-1-methyl-1H-pyrazole hydrochloride (486 mg), potassium hydroxide (337 mg), Pd(dppf)Cl$_2$ DCM (82.0 mg) and water (1 ml), and the mixture was stirred under microwave radiation at 80° C. for 15 min. To the reaction mixture was added water and the mixture was extracted with ethyl acetate. The obtained organic layer was washed with water and saturated brine, dried over anhydrous sodium sulfate, and the solvent was evaporated under reduced pressure. The residue was purified by silica gel column chromatography (ethyl acetate/hexane) to give the title compound (157 mg).
MS (ESI+): [M+H]$^+$ 356.0.

C) 1,5-anhydro-2-(((5-chloro-6-methyl-4-(4-(1-methyl-1H-pyrazol-3-yl)benzyl)pyridin-2-yl)carbonyl)amino)-2,4-dideoxy-L-threo-pentitol The title compound was obtained by a method similar to that in Example 1, Steps F, G.

Example 101

1,5-anhydro-2-(((5-chloro-4-(4-cyanobenzyl)-6-methylpyridin-2-yl)carbonyl)amino)-2,4-dideoxy-L-threo-pentitol

A) methyl 5-chloro-6-methyl-4-(4,4,5,5-tetramethyl-1,3,2-dioxaborolan-2-yl)picolinate 4,4,4',4',5,5,5',5'-Octamethyl-2,2'-bi-1,3,2-dioxaborolane (279 mg), di-mu-methoxobis(1,5-cyclooctadiene)diiridium (I) (19.9 mg) and 4,4'-di-tert-butyl-2,2'-bipyridine (8.05 mg) were stirred in tert-butyl methyl ether (4 ml) at room temperature for 5 min. Methyl 5-chloro-6-methylpicolinate (186 mg) was added, and the mixture was stirred under microwave radiation at 90° C. for 1 hr. The reaction mixture was purified by silica gel column chromatography (ethyl acetate/hexane) to give the title compound (206 mg).
$^1$H NMR (300 MHz, DMSO-d$_6$) δ1.33 (12H, s), 2.61 (3H, s), 3.88 (3H, s), 8.03 (1H, s).

B) 1,5-anhydro-2-(((5-chloro-4-(4-cyanobenzyl)-6-methylpyridin-2-yl)carbonyl)amino)-2,4-dideoxy-L-threo-pentitol The title compound was obtained by a method similar to that in Example 1, Steps E-G.

Example 104

5-chloro-4-((6-cyanopyridin-3-yl)methyl)-N-((1S,2S)-2-hydroxycyclohexyl)-6-methylpyridine-2-carboxamide 5-Chloro-4-((6-chloropyridin-3-yl)methyl)-N-((1S,2S)-2-hydroxycyclohexyl)-6-methylpicolinamide (90.0 mg), Pd(Ph$_3$P)$_4$ (52.8 mg) and zinc cyanide (26.8 mg) were stirred in DMF (1 mL) under microwave radiation at 120° C. for 3 hr. To the reaction mixture were added water and ethyl acetate, and the mixture was filtered through celite. The obtained organic layer was washed with saturated brine, dried over anhydrous magnesium sulfate, and the solvent was evaporated under reduced pressure. The residue was purified by silica gel column chromatography (ethyl acetate/hexane) to give the title compound (28.5 mg).
$^1$H NMR (300 MHz, DMSO-d$_6$) δ1.19-1.38 (4H, m), 1.64 (2H, d, J=5.5 Hz), 1.82-1.95 (2H, m), 2.64 (3H, s), 3.41-3.64 (2H, m), 4.35 (2H, s), 4.69 (1H, d, J=5.5 Hz), 7.84-7.92 (2H, m), 7.99 (1H, d, J=7.9 Hz), 8.28 (1H, d, J=8.1 Hz), 8.71 (1H, s).

Example 107

5-chloro-N-((1S,2S)-2-hydroxycyclohexyl)-6-methyl-4-((6-(1-methyl-1H-pyrazol-3-yl)pyridin-3-yl)methyl)pyridine-2-carboxamide

A) methyl 5-chloro-6-methyl-4-((6-(1-methyl-1H-pyrazol-3-yl)pyridin-3-yl)methyl)picolinate Methyl 5-chloro-4-((6-chloropyridin-3-yl)methyl)-6-methylpicolinate (100 mg), 1-methyl-3-(4,4,5,5-tetramethyl-1,3,2-dioxaborolan-2-yl)-1H-pyrazole (100 mg), sodium carbonate (68.1 mg) and Pd(Ph$_3$P)$_4$ (18.6 mg) were stirred in a mixture of DME (1.5 mL) and water (0.3 mL) under a nitrogen atmosphere at 80° C. overnight. The reaction mixture was diluted with water, and extracted twice with ethyl acetate. The obtained organic layer was washed with saturated brine, dried over anhydrous magnesium sulfate, and the solvent was evaporated under reduced pressure. The residue was purified by HPLC to give the title compound (32.7 mg).
MS (ESI+): [M+H]$^+$ 357.0.

B) 5-chloro-N-((1S,2S)-2-hydroxycyclohexyl)-6-methyl-4-((6-(1-methyl-1H-pyrazol-3-yl)pyridin-3-yl)methyl)pyridine-2-carboxamide The title compound was obtained by a method similar to that in Example 1, Steps F and G.

Example 112

5-cyano-N-((1S,2S)-2-hydroxycyclohexyl)-6-methyl-4-(4-(1H-pyrazol-1-yl)benzyl)pyridine-2-carboxamide

A) methyl 4-(4-(1H-pyrazol-1-yl)benzyl)-5-cyano-6-methylpicolinate

Methyl 5-cyano-6-methylpicolinate (100 mg), 4,4,4',4',5,5,5',5'-octamethyl-2,2'-bi-1,3,2-dioxaborolane (147 mg), di-mu-methoxobis(1,5-cyclooctadiene)diiridium(I) (37.6 mg) and 4,4'-di-tert-butyl-2,2'-bipyridine (15.6 mg) were stirred in tert-butyl methyl ether (3 ml) under microwave radiation at 80° C. for 1 hr. The reaction mixture was added to water, and the mixture was extracted twice with ethyl acetate. The combined organic layer was washed with saturated brine, dried over anhydrous sodium sulfate, and the solvent was evaporated under reduced pressure. To a solution of the obtained residue in DMF (2.8 ml) were added 1-(4-(chloromethyl)phenyl)-1H-pyrazole (109 mg), tripotassium phosphate (381 mg) and Pd(dppf)Cl$_2$ DCM (47.3 mg), and the mixture was stirred under microwave radiation at 80° C. for 30 min. The reaction mixture was added to water and the mixture was extracted twice with ethyl acetate. The combined organic layer was washed with water and saturated brine, dried over anhydrous sodium sulfate, and the solvent was evaporated under reduced pressure. The residue was purified by silica gel column chromatography (ethyl acetate/hexane) to give the title compound (37.0 mg).
MS (ESI+): [M+H]$^+$ 333.0.

B) 4-(4-(1H-pyrazol-1-yl)benzyl)-5-cyano-6-methylpicolinic Acid

A mixed solution of methyl 4-(4-(1H-pyrazol-1-yl)benzyl)-5-cyano-6-methylpicolinate (34.5 mg), 2 M aqueous sodium hydroxide solution (0.2 mL) in THF (2.5 mL) and methanol (2.5 mL) was stirred at 60° C. for 1 hr. After cooling, to the reaction mixture was added 2 M hydrochloric acid (0.4 mL) at 0° C., and the solvent was evaporated under reduced pressure to give the title compound. This was used for the next step without further purification.
MS (ESI+): [M+H]$^+$ 319.0.

C) 4-(4-(1H-pyrazol-1-yl)benzyl)-5-cyano-N-((1S,2S)-2-hydroxycyclohexyl)-6-methylpicolinamide To a solution of 4-(4-(1H-pyrazol-1-yl)benzyl)-5-cyano-6-methylpicolinic acid obtained in the previous step, (1S,2S)-2-aminocyclohexanol (14.6 mg), WSC (26.4 mg), HOBt monohydrate (21.3 mg) in DMF (2 mL) was added triethylamine (42.4 mg), and the mixture was stirred at room temperature overnight. The reaction mixture was diluted with water, and extracted twice with ethyl acetate. The combined organic layer was washed with water and saturated brine, dried over anhydrous sodium sulfate, and the solvent was evaporated under reduced pressure. The residue was purified by silica gel column chromatography (ethyl acetate/hexane). The obtained oil was dissolved in ethyl acetate, washed with saturated aqueous sodium hydrogen carbonate solution and saturated brine, dried over anhydrous sodium sulfate, and the solvent was evaporated under reduced pressure. The obtained residue was recrystallized from hexane/ethyl acetate to give the title compound (21.2 mg).
$^1$H NMR (300 MHz, CDCl$_3$) δ1.22-1.49 (4H, m), 1.78 (2H, brs), 2.07 (2H, d, J=13.8 Hz), 2.81 (3H, s), 2.90-2.96 (1H, m), 3.51 (1H, dd, J=9.7, 4.7 Hz), 3.82 (1H, brs), 4.25 (2H, s), 6.46 (1H, s), 7.33 (2H, d, J=8.3 Hz), 7.66 (2H, d, J=8.2 Hz), 7.71 (1H, s), 7.90 (1H, s), 7.96-8.03 (2H, m).

The compounds and intermediates of Examples 5, 7, 9, 11, 13, 15-18, 21-33, 35, 36, 38-42, 44-52, 54, 55, 59-63, 66, 69-71, 75-83, 85, 86, 88-93, 95, 97-100, 102, 103, 105, 106, 108-111, 113-117 in the following Tables were produced according to the methods shown in the above-mentioned Examples or methods analogous thereto. The Example compounds are shown in the following Tables. MS in the Tables shows measured values.

TABLE 1-1

| Ex. No. | IUPAC name | structural formula | salt | MS |
|---|---|---|---|---|
| 1 | N-((1S,2S)-2-hydroxycyclopentyl)-5-methyl-4-(4-(1-methyl-1H-pyrazol-3-yl)benzyl)pyridine-2-carboxamide | | | 391.1 |

TABLE 1-1-continued

| Ex. No. | IUPAC name | structural formula | salt | MS |
|---|---|---|---|---|
| 2 | 1,5-anhydro-2,4-dideoxy-2-(((5-methyl-4-(4-(1-methyl-1H-pyrazol-3-yl)benzyl)pyridin-2-yl)carbonyl)amino)-L-threo-pentitol | | | 407.2 |
| 4 | N-((1S,2S)-2-hydroxycyclohexyl)-5-methyl-4-(4-(1H-pyrazol-1-yl)benzyl)pyridine-2-carboxamide | | | 391.2 |
| 5 | N-((1S,2S)-2-hydroxycyclopentyl)-5-methyl-4-(4-(1H-pyrazol-1-yl)benzyl)pyridine-2-carboxamide | | | 377.2 |
| 6 | 5-chloro-N-((1S,2S)-2-hydroxycyclohexyl)-4-(4-(1H-pyrazol-1-yl)benzyl)pyridine-2-carboxamide | | | 411.0 |

TABLE 1-1-continued

| Ex. No. | IUPAC name | structural formula | salt | MS |
|---|---|---|---|---|
| 7 | 5-chloro-N-((1S,2S)-2-hydroxycyclopentyl)-4-(4-(1H-pyrazol-1-yl)benzyl)pyridine-2-carboxamide | | | 397.2 |
| 8 | 1,5-anhydro-2-(((5-chloro-4-(4-(1H-pyrazol-1-yl)benzyl)pyridin-2-yl)carbonyl)amino)-2,4-dideoxy-L-threo-pentitol | | HCl | 413.0 |

TABLE 1-2

| Ex. No. | IUPAC name | structural formula | salt | MS |
|---|---|---|---|---|
| 9 | N-((1S,2S)-2-hydroxycyclohexyl)-5-methyl-4-(4-(1-methyl-1H-pyrazol-3-yl)benzyl)pyridine-2-carboxamide | | | 405.2 |
| 10 | 4-(2-fluoro-4-(1-methyl-1H-pyrazol-3-yl)benzyl)-N-((1S,2S)-2-hydroxycyclohexyl)-5-methylpyridine-2-carboxamide | | | 423.1 |

TABLE 1-2-continued

| Ex. No. | IUPAC name | structural formula | salt | MS |
|---|---|---|---|---|
| 11 | 4-(2-fluoro-4-(1-methyl-1H-pyrazol-3-yl)benzyl)-N-((1S,2S)-2-hydroxycyclopentyl)-5-methylpyridine-2-carboxamide | | | 409.1 |
| 12 | 4-(2-fluoro-4-(1H-pyrazol-1-yl)benzyl)-N-((1S,2S)-2-hydroxycyclohexyl)-5-methylpyridine-2-carboxamide | | | 409.0 |
| 13 | 4-(2-fluoro-4-(1H-pyrazol-1-yl)benzyl)-N-((1S,2S)-2-hydroxycyclopentyl)-5-methylpyridine-2-carboxamide | | | 395.1 |
| 14 | 4-(4-(1,3-dimethyl-1H-pyrazol-4-yl)benzyl)-N-((1S,2S)-2-hydroxycyclopentyl)-5-methylpyridine-2-carboxamide | | 2HCl | 405.1 |

TABLE 1-2-continued

| Ex. No. | IUPAC name | structural formula | salt | MS |
|---|---|---|---|---|
| 15 | 4-(4-(1,3-dimethyl-1H-pyrazol-4-yl)benzyl)-N-((1S,2S)-2-hydroxycyclohexyl)-5-methylpyridine-2-carboxamide | | 2HCl | 419.1 |
| 16 | 1,5-anhydro-2,4-dideoxy-2-(((4-(2-fluoro-4-(1-methyl-1H-pyrazol-3-yl)benzyl)-5-methylpyridin-2-yl)carbonyl)amino)-L-threo-pentitol | | | 425.1 |

TABLE 1-3

| Ex. No. | IUPAC name | structural formula | salt | MS |
|---|---|---|---|---|
| 17 | 1,5-anhydro-2,4-dideoxy-2-(((4-(2-fluoro-4-(1H-pyrazol-1-yl)benzyl)-5-methylpyridin-2-yl)carbonyl)amino)-L-threo-pentitol | | | 411.2 |
| 18 | N-(2-methoxycyclohexyl)-5-methyl-4-(4-(1-methyl-1H-pyrazol-3-yl)benzyl)pyridine-2-carboxamide | | | 419.1 |

TABLE 1-3-continued

| Ex. No. | IUPAC name | structural formula | salt | MS |
|---|---|---|---|---|
| 19 | N-((1S,2S)-2-hydroxycyclohexyl)-4-(4-methoxybenzyl)-5-methylpyridine-2-carboxamide | | | 355.2 |
| 20 | N-(1-(hydroxymethyl)cyclopentyl)-5-methyl-4-(4-(1-methyl-1H-pyrazol-3-yl)benzyl)pyridine-2-carboxamide | | | 405.2 |
| 21 | 1,5-anhydro-2,3-dideoxy-3-(((5-methyl-4-(4-(1-methyl-1H-pyrazol-3-yl)benzyl)pyridin-2-yl)carbonyl)amino)pentitol | | | 407.2 |
| 22 | N-(2,2-difluorocyclopropyl)-5-methyl-4-(4-(1-methyl-1H-pyrazol-3-yl)benzyl)pyridine-2-carboxamide | | | 383.2 |

TABLE 1-3-continued

| Ex. No. | IUPAC name | structural formula | salt | MS |
|---|---|---|---|---|
| 23 | N-(1-(hydroxymethyl)cyclopropyl)-5-methyl-4-(4-(1-methyl-1H-pyrazol-3-yl)benzyl)pyridine-2-carboxamide | | | 377.3 |
| 24 | N-((1S,2R)-2-hydroxy-2,3-dihydro-1H-inden-1-yl)-5-methyl-4-(4-(1-methyl-1H-pyrazol-3-yl)benzyl)pyridine-2-carboxamide | | | 439.2 |

TABLE 1-4

| Ex. No. | IUPAC name | structural formula | salt | MS |
|---|---|---|---|---|
| 25 | N-(5,5-difluoro-2-hydroxycyclohexyl)-5-methyl-4-(4-(1-methyl-1H-pyrazol-3-yl)benzyl)pyridine-2-carboxamide | | | 441.2 |

TABLE 1-4-continued
| Ex. No. | IUPAC name | structural formula | salt | MS |
|---|---|---|---|---|
| 26 | 5-methyl-4-(4-(1-methyl-1H-pyrazol-3-yl)benzyl)-N-(oxetan-3-yl)pyridine-2-carboxamide | 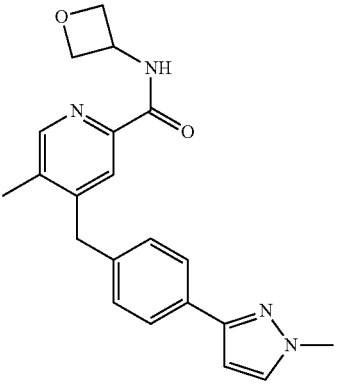 | | 363.3 |
| 27 | 5-methyl-4-(4-(1-methyl-1H-pyrazol-3-yl)benzyl)-N-(tetrahydro-2H-pyran-4-yl)pyridine-2-carboxamide | 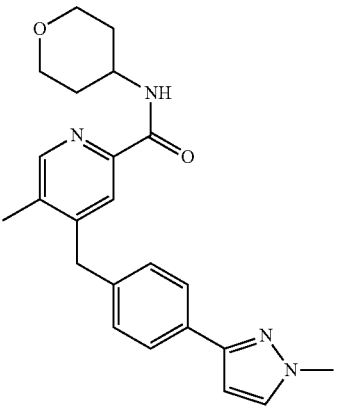 | | 391.2 |
| 28 | N-cyclopropyl-5-methyl-4-(4-(1-methyl-1H-pyrazol-3-yl)benzyl)pyridine-2-carboxamide | 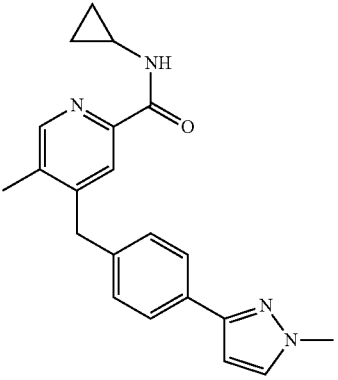 | | 347.3 |
| 29 | N-cyclobutyl-5-methyl-4-(4-(1-methyl-1H-pyrazol-3-yl)benzyl)pyridine-2-carboxamide | 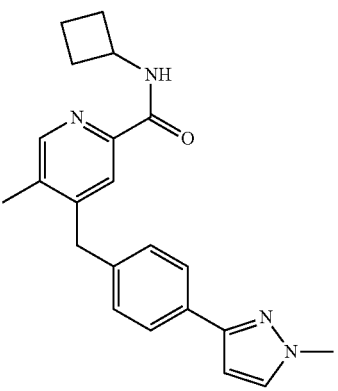 | | 361.2 |

TABLE 1-4-continued
| Ex. No. | IUPAC name | structural formula | salt | MS |
|---|---|---|---|---|
| 30 | N-(3,3-difluorocyclobutyl)-5-methyl-4-(4-(1-methyl-1H-pyrazol-3-yl)benzyl)pyridine-2-carboxamide | 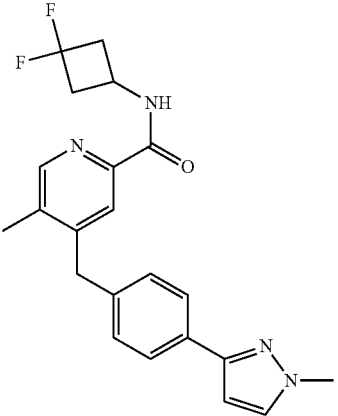 | | 397.2 |
| 31 | 5-methyl-4-(4-(1-methyl-1H-pyrazol-3-yl)benzyl)-N-(tetrahydrofuran-3-yl)pyridine-2-carboxamide | 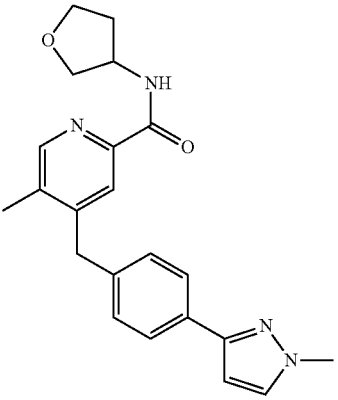 | | 377.3 |
| 32 | 5-methyl-4-(4-(1-methyl-1H-pyrazol-3-yl)benzyl)-N-(tetrahydro-2H-pyran-3-yl)pyridine-2-carboxamide | 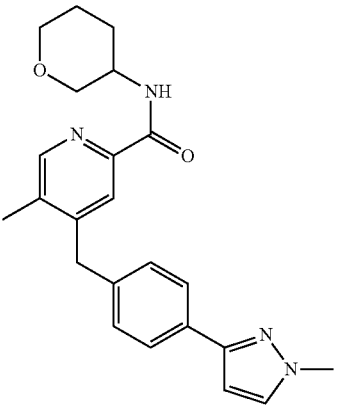 | | 391.2 |

TABLE 1-5

| Ex. No. | IUPAC name | structural formula | salt | MS |
|---|---|---|---|---|
| 33 | N-(4,4-difluorocyclohexyl)-5-methyl-4-(4-(1-methyl-1H-pyrazol-3-yl)benzyl)pyridine-2-carboxamide | | | 425.2 |
| 34 | N-((1S,2S)-2-hydroxycyclopentyl)-5-methyl-4-((6-(1H-pyrazol-1-yl)pyridin-3-yl)methyl)pyridine-2-carboxamide | | | 378.2 |
| 35 | N-((1S,2S)-2-hydroxycyclohexyl)-5-methyl-4-((6-(1H-pyrazol-1-yl)pyridin-3-yl)methyl)pyridine-2-carboxamide | | | 392.2 |
| 36 | 1,5-anhydro-2,4-dideoxy-2-(((4-(2-fluoro-4-(1H-pyrazol-1-yl)benzyl)-5-methylpyridin-2-yl)carbonyl)amino)-L-threo-pentitol | | | 411.1 |

TABLE 1-5-continued

| Ex. No. | IUPAC name | structural formula | salt | MS |
|---|---|---|---|---|
| 37 | 5-(difluoromethyl)-N-((1S,2S)-2-hydroxycyclopentyl)-4-(4-(1H-pyrazol-1-yl)benzyl)pyridine-2-carboxamide | | | 413.1 |
| 38 | 5-(difluoromethyl)-N-((1S,2S)-2-hydroxycyclohexyl)-4-(4-(1H-pyrazol-1-yl)benzyl)pyridine-2-carboxamide | | | 427.2 |
| 39 | 1,5-anhydro-2,4-dideoxy-2-(((5-(difluoromethyl)-4-(4-(1H-pyrazol-1-yl)benzyl)pyridin-2-yl)carbonyl)amino)-L-threo-pentitol | | HCl | 429.1 |
| 40 | 1,5-anhydro-2,4-dideoxy-2-(((5-(difluoromethyl)-4-(4-(1-methyl-1H-pyrazol-3-yl)benzyl)pyridin-2-yl)carbonyl)amino)-L-threo-pentitol | | | 443.2 |

TABLE 1-6

| Ex. No. | IUPAC name | structural formula | salt | MS |
|---|---|---|---|---|
| 41 | 5-(difluoromethyl)-N-((1S,2S)-2-hydroxycyclohexyl)-4-(4-(1-methyl-1H-pyrazol-3-yl)benzyl)pyridine-2-carboxamide | | | 441.2 |
| 42 | N-((1S,2S)-2-hydroxycyclohexyl)-4-(4-(1H-pyrazol-1-yl)benzyl)-5-vinylpyridine-2-carboxamide | | | 403.1 |
| 43 | 5-ethyl-N-((1S,2S)-2-hydroxycyclohexyl)-4-(4-(1H-pyrazol-1-yl)benzyl)pyridine-2-carboxamide | | | 405.1 |
| 44 | 1,5-anhydro-2,4-dideoxy-2-(((5-ethyl-4-(4-(1H-pyrazol-1-yl)benzyl)pyridin-2-yl)carbonyl)amino)-L-threo-pentitol | | | 407.1 |

TABLE 1-6-continued

| Ex. No. | IUPAC name | structural formula | salt | MS |
|---|---|---|---|---|
| 45 | N-((1S,2S)-2-hydroxycyclohexyl)-4-(4-(1H-pyrazol-1-yl)benzyl)pyridine-2-carboxamide | | | 377.1 |
| 46 | 5-cyclopropyl-N-((1S,2S)-2-hydroxycyclohexyl)-4-(4-(1H-pyrazol-1-yl)benzyl)pyridine-2-carboxamide | | | 417.2 |
| 47 | 1,5-anhydro-2-(((5-cyclopropyl-4-(4-(1H-pyrazol-1-yl)benzyl)pyridin-2-yl)carbonyl)amino)-2,4-dideoxy-L-threo-pentitol | | | 419.2 |
| 48 | N-((1S,2S)-2-hydroxycyclohexyl)-5-methyl-4-(4-(1H-pyrazol-1-yl)benzyl)pyridine-2-carboxamide | | | 391.1 |

TABLE 1-7

| Ex. No. | IUPAC name | structural formula | salt | MS |
|---|---|---|---|---|
| 49 | 1,5-anhydro-2,4-dideoxy-2-(((5-methyl-4-(4-(1H-pyrazol-1-yl)benzyl)pyridin-2-yl)carbonyl)amino)-L-threo-pentitol | | | 393.1 |
| 50 | N-((1S,2S)-2-hydroxycyclopentyl)-5-methyl-4-(4-(1H-pyrazol-1-yl)benzyl)pyridine-2-carboxamide | | | 377.2 |
| 51 | 5-chloro-N-((1S,2S)-2-hydroxycyclohexyl)-4-(4-(1-methyl-1H-pyrazol-3-yl)benzyl)pyridine-2-carboxamide | | | 425.0 |
| 52 | 5-chloro-N-((1S,2S)-2-hydroxycyclohexyl)-4-(4-(1-methyl-1H-pyrazol-3-yl)benzyl)pyridine-2-carboxamide | | HCl | 425.1 |

TABLE 1-7-continued

| Ex. No. | IUPAC name | structural formula | salt | MS |
|---|---|---|---|---|
| 53 | 5-chloro-4-(2-fluoro-4-(1H-pyrazol-1-yl)benzyl)-N-((1S,2S)-2-hydroxycyclopentyl)pyridine-2-carboxamide | | | 415.1 |
| 54 | 5-chloro-4-(2-fluoro-4-(1H-pyrazol-1-yl)benzyl)-N-((1S,2S)-2-hydroxycyclohexyl)pyridine-2-carboxamide | | | 429.1 |
| 55 | 5-fluoro-N-((1S,2S)-2-hydroxycyclohexyl)-4-(4-(1H-pyrazol-1-yl)benzyl)pyridine-2-carboxamide | | | 395.2 |
| 56 | 1,5-anhydro-2,4-dideoxy-2-(((5-methoxy-4-(4-(1H-pyrazol-1-yl)benzyl)pyridin-2-yl)carbonyl)amino)-L-threo-pentitol | | | 409.2 |

TABLE 1-8

| Ex. No. | IUPAC name | structural formula | salt | MS |
|---|---|---|---|---|
| 57 | 4-((6-chloropyridin-3-yl)methyl)-N-((1S,2S)-2-hydroxycyclohexyl)-5-methoxypyridine-2-carboxamide | | | 376.1 |
| 58 | N-((1S,2S)-2-hydroxycyclohexyl)-5-methoxy-4-((6-(1-methyl-1H-pyrazol-4-yl)pyridin-3-yl)methyl)pyridine-2-carboxamide | | | 422.1 |
| 59 | N-((1S,2S)-2-hydroxycyclohexyl)-5-methoxy-4-((6-(1-methyl-1H-pyrazol-4-yl)pyridin-3-yl)methyl)pyridine-2-carboxamide | | | 422.2 |
| 60 | N-((1S,2S)-2-hydroxycyclopentyl)-5-methoxy-4-(4-(1H-pyrazol-1-yl)benzyl)pyridine-2-carboxamide | | | 393.2 |

TABLE 1-8-continued

| Ex. No. | IUPAC name | structural formula | salt | MS |
|---|---|---|---|---|
| 61 | 4-((6-chloropyridin-3-yl)methyl)-N-((1S,2S)-2-hydroxycyclohexyl)-5-methoxypyridine-2-carboxamide | | | 376.0 |
| 62 | 4-(4-bromobenzyl)-N-((1S,2S)-2-hydroxycyclohexyl)-5-methoxypyridine-2-carboxamide | | | 419.1 |
| 63 | N-((1S,2S)-2-Hydroxycyclohexyl)-5-methoxy-4-(4-(1H-pyrazol-1-yl)benzyl)pyridine-2-carboxamide | | | 407.2 |
| 64 | N-((1S,2S)-2-hydroxycyclohexyl)-5-methoxy-4-(4-(1-methyl-1H-pyrazol-4-yl)benzyl)pyridine-2-carboxamide | | | 421.2 |

TABLE 1-9

| Ex. No. | IUPAC name | structural formula | salt | MS |
|---|---|---|---|---|
| 65 | 5-chloro-N-((1S,2S)-2-hydroxycyclohexyl)-6-methyl-4-(4-(1-methyl-1H-pyrazol-3-yl)benzyl)pyridine-2-carboxamide | | | 439.2 |
| 66 | 5-chloro-4-(4-cyanobenzyl)-N-((1S,2S)-2-hydroxycyclohexyl)-6-methylpyridine-2-carboxamide | | | 384.1 |
| 67 | 5-cyano-N-((1S,2S)-2-hydroxycyclohexyl)-4-(4-(1H-pyrazol-1-yl)benzyl)pyridine-2-carboxamide | | | 402.1 |
| 68 | N-((1S,2S)-2-hydroxycyclopentyl)-6-methoxy-4-(4-(1H-pyrazol-1-yl)benzyl)pyridine-2-carboxamide | | | 393.2 |

TABLE 1-9-continued

| Ex. No. | IUPAC name | structural formula | salt | MS |
|---|---|---|---|---|
| 69 | N-((1S,2S)-2-hydroxycyclohexyl)-6-methoxy-4-(4-(1H-pyrazol-1-yl)benzyl)pyridine-2-carboxamide | | | 407.2 |
| 70 | N-((1S,2S)-2-hydroxycyclohexyl)-6-methyl-4-(4-(1H-pyrazol-1-yl)benzyl)pyridine-2-carboxamide | | | 391.2 |
| 71 | N-((1S,2S)-2-hydroxycyclohexyl)-4-(4-methoxybenzyl)-6-methylpyridine-2-carboxamide | | | 355.2 |
| 72 | N-((1S,2S)-2-hydroxycyclopentyl)-5,6-dimethyl-4-(4-(1-methyl-1H-pyrazol-3-yl)benzyl)pyridine-2-carboxamide | | | 405.2 |

TABLE 1-10

| Ex. No. | IUPAC name | structural formula | salt | MS |
|---|---|---|---|---|
| 73 | 4-((6-chloropyridin-3-yl)methyl)-N-((1S,2S)-2-hydroxycyclohexyl)-5,6-dimethylpyridine-2-carboxamide | | | 374.1 |
| 74 | N-((1S,2S)-2-hydroxycyclohexyl)-5,6-dimethyl-4-((6-(1-methyl-1H-pyrazol-3-yl)pyridin-3-yl)methyl)pyridine-2-carboxamide | | | 420.3 |
| 75 | N-((1S,2S)-2-hydroxycyclopentyl)-5,6-dimethyl-4-(4-(1H-pyrazol-1-yl)benzyl)pyridine-2-carboxamide | | | 391.2 |
| 76 | N-((1S,2S)-2-hydroxycyclohexyl)-5,6-dimethyl-4-(4-(1H-pyrazol-1-yl)benzyl)pyridine-2-carboxamide | | | 405.2 |

TABLE 1-10-continued

| Ex. No. | IUPAC name | structural formula | salt | MS |
|---|---|---|---|---|
| 77 | 4-(4-bromobenzyl)-N-((1S,2S)-2-hydroxycyclohexyl)-5,6-dimethylpyridine-2-carboxamide | | | 417.0 |
| 78 | 1,5-anhydro-2,4-dideoxy-2-(((5,6-dimethyl-4-(4-(1H-pyrazol-1-yl)benzyl)pyridin-2-yl)carbonyl)amino)-L-threo-pentitol | | | 407.2 |
| 79 | N-((1S,2S)-2-hydroxycyclohexyl)-5,6-dimethyl-4-(4-(1-methyl-1H-pyrazol-4-yl)benzyl)pyridine-2-carboxamide | | | 419.2 |
| 80 | N-((1S,2S)-2-hydroxycyclohexyl)-5,6-dimethyl-4-((6-(1-methyl-1H-pyrazol-4-yl)pyridin-3-yl)methyl)pyridine-2-carboxamide | | | 420.2 |

TABLE 1-11

| Ex. No. | IUPAC name | structural formula | salt | MS |
|---|---|---|---|---|
| 81 | N-((1S,2S)-2-hydroxycyclohexyl)-5,6-dimethyl-4-(4-(1-methyl-1H-pyrazol-3-yl)benzyl)pyridine-2-carboxamide | | | 419.2 |
| 82 | 1,5-anhydro-2,4-dideoxy-2-(((5,6-dimethyl-4-(4-(1-methyl-1H-pyrazol-3-yl)benzyl)pyridin-2-yl)carbonyl)amino)-L-threo-pentitol | | | 421.2 |
| 83 | 1,5-anhydro-2,4-dideoxy-2-(((4-(4-methoxybenzyl)-5,6-dimethylpyridin-2-yl)carbonyl)amino)-L-threo-pentitol | | | 371.2 |
| 84 | N-((1S,2S)-2-hydroxycyclohexyl)-5,6-dimethyl-4-((6-methylpyridin-3-yl)methyl)pyridine-2-carboxamide | | | 354.2 |

TABLE 1-11-continued

| Ex. No. | IUPAC name | structural formula | salt | MS |
|---|---|---|---|---|
| 85 | 1,5-anhydro-2-(((4-((6-chloropyridin-3-yl)methyl)-5,6-dimethylpyridin-2-yl)carbonyl)amino)-2,4-dideoxy-L-threo-pentitol | | | 376.1 |
| 86 | 1,5-anhydro-2,4-dideoxy-2-(((5,6-dimethyl-4-((6-(1-methyl-1H-pyrazol-3-yl)pyridin-3-yl)methyl)pyridin-2-yl)carbonyl)amino)-L-threo-pentitol | | | 422.2 |
| 87 | 1,5-anhydro-2,4-dideoxy-2-(((6-methoxy-5-methyl-4-(4-(1-methyl-1H-pyrazol-3-yl)benzyl)pyridin-2-yl)carbonyl)amino)-L-threo-pentitol | | | 437.2 |
| 88 | N-((1S,2S)-2-hydroxycyclohexyl)-6-methoxy-5-methyl-4-(4-(1-methyl-1H-pyrazol-3-yl)benzyl)pyridine-2-carboxamide | | | 435.2 |

TABLE 1-12

| Ex. No. | IUPAC name | structural formula | salt | MS |
|---|---|---|---|---|
| 89 | 1,5-anhydro-2,4-dideoxy-2-(((6-methoxy-5-methyl-4-(4-(1-methyl-1H-pyrazol-3-yl)benzyl)pyridin-2-yl)carbonyl)amino)-L-threo-pentitol | | HCl | 437.2 |
| 90 | N-((1S,2S)-2-hydroxycyclopentyl)-6-methoxy-5-methyl-4-(4-(1-methyl-1H-pyrazol-3-yl)benzyl)pyridine-2-carboxamide | | HCl | 421.2 |
| 91 | N-((1S,2S)-2-hydroxycyclohexyl)-6-methoxy-5-methyl-4-(4-(1H-pyrazol-1-yl)benzyl)pyridine-2-carboxamide | | | 421.2 |
| 92 | 1,5-anhydro-2,4-dideoxy-2-(((6-methoxy-5-methyl-4-(4-(1H-pyrazol-1-yl)benzyl)pyridin-2-yl)carbonyl)amino)-L-threo-pentitol | | | 423.2 |

TABLE 1-12-continued

| Ex. No. | IUPAC name | structural formula | salt | MS |
|---|---|---|---|---|
| 93 | N-((1S,2S)-2-hydroxycyclopentyl)-6-methoxy-5-methyl-4-(4-(1H-pyrazol-1-yl)benzyl)pyridine-2-carboxamide | | | 407.2 |
| 94 | 5-(difluoromethoxy)-N-((1S,2S)-2-hydroxycyclohexyl)-4-(4-(1H-pyrazol-1-yl)benzyl)pyridine-2-carboxamide | | | 443.2 |
| 95 | 1,5-anhydro-2,4-dideoxy-2-(((5-(difluoromethoxy)-4-(4-(1H-pyrazol-1-yl)benzyl)pyridin-2-yl)carbonyl)amino)-L-threo-pentitol | | | 445.2 |
| 96 | 1,5-anhydro-2-(((5-chloro-6-methyl-4-(4-(1-methyl-1H-pyrazol-3-yl)benzyl)pyridin-2-yl)carbonyl)amino)-2,4-dideoxy-L-threo-pentitol | | | 441.1 |

TABLE 1-13

| Ex. No. | IUPAC name | structural formula | salt | MS |
|---|---|---|---|---|
| 97 | 5-chloro-N-((1S,2S)-2-hydroxycyclopentyl)-6-methyl-4-(4-(1-methyl-1H-pyrazol-3-yl)benzyl)pyridine-2-carboxamide | | | 425.1 |
| 98 | 5-chloro-N-((1S,2S)-2-hydroxycyclohexyl)-6-methyl-4-(4-(1H-pyrazol-1-yl)benzyl)pyridine-2-carboxamide | | | 425.1 |
| 99 | 1,5-anhydro-2-(((5-chloro-6-methyl-4-(4-(1H-pyrazol-1-yl)benzyl)pyridin-2-yl)carbonyl)amino)-2,4-dideoxy-L-threo-pentitol | | | 427.2 |
| 100 | 5-chloro-N-((1S,2S)-2-hydroxycyclopentyl)-6-methyl-4-(4-(1H-pyrazol-1-yl)benzyl)pyridine-2-carboxamide | | | 411.1 |

TABLE 1-13-continued

| Ex. No. | IUPAC name | structural formula | salt | MS |
|---|---|---|---|---|
| 101 | 1,5-anhydro-2-(((5-chloro-4-(4-cyanobenzyl)-6-methylpyridin-2-yl)carbonyl)amino)-2,4-dideoxy-L-threo-pentitol | | | 386.1 |
| 102 | 1,5-anhydro-2-(((5-chloro-4-(4-methoxybenzyl)-6-methylpyridin-2-yl)carbonyl)amino)-2,4-dideoxy-L-threo-pentitol | | | 391.1 |
| 103 | 5-chloro-4-((6-chloropyridin-3-yl)methyl)-N-((1S,2S)-2-hydroxycyclohexyl)-6-methylpyridine-2-carboxamide | | | 394.1 |
| 104 | 5-chloro-4-((6-cyanopyridin-3-yl)methyl)-N-((1S,2S)-2-hydroxycyclohexyl)-6-methylpyridine-2-carboxamide | | | 385.1 |

TABLE 1-14

| Ex. No. | IUPAC name | structural formula | salt | MS |
|---|---|---|---|---|
| 105 | 5-chloro-N-((1S,2S)-2-hydroxycyclohexyl)-4-((6-methoxypyridin-3-yl)methyl)-6-methylpyridine-2-carboxamide | | | 390.2 |
| 106 | 1,5-anhydro-2-(((5-chloro-4-((6-methoxypyridin-3-yl)methyl)-6-methylpyridin-2-yl)carbonyl)amino)-2,4-dideoxy-L-threo-pentitol | | | 392.1 |
| 107 | 5-chloro-N-((1S,2S)-2-hydroxycyclohexyl)-6-methyl-4-((6-(1-methyl-1H-pyrazol-3-yl)pyridin-3-yl)methyl)pyridine-2-carboxamide | | | 440.1 |
| 108 | 5-chloro-4-((6-(1-ethyl-1H-pyrazol-4-yl)pyridin-3-yl)methyl)-N-((1S,2S)-2-hydroxycyclohexyl)-6-methylpyridine-2-carboxamide | | | 454.3 |

| Ex. No. | IUPAC name | structural formula | salt | MS |
|---|---|---|---|---|
| 109 | 5-chloro-4-((6-(1,3-dimethyl-1H-pyrazol-4-yl)pyridin-3-yl)methyl)-N-((1S,2S)-2-hydroxycyclohexyl)-6-methylpyridine-2-carboxamide | | | 454.2 |
| 110 | 5-chloro-N-((1S,2S)-2-hydroxycyclohexyl)-6-methyl-4-((6-methylpyridin-3-yl)methyl)pyridine-2-carboxamide | | HCl | 374.1 |
| 111 | 1,5-anhydro-2-(((5-chloro-6-methyl-4-((6-methylpyridin-3-yl)methyl)pyridin-2-yl)carbonyl)amino)-2,4-dideoxy-L-threo-pentitol | | | 376.1 |
| 112 | 5-cyano-N-((1S,2S)-2-hydroxycyclohexyl)-6-methyl-4-(4-(1H-pyrazol-1-yl)benzyl)pyridine-2-carboxamide | | | 416.2 |

TABLE 1-15

| Ex. No. | IUPAC name | structural formula | salt | MS |
|---|---|---|---|---|
| 113 | 1,5-anhydro-2-(((5-cyano-6-methyl-4-(4-(1H-pyrazol-1-yl)benzyl)pyridin-2-yl)carbonyl)amino)-2,4-dideoxy-L-threo-pentitol | | | 418.1 |
| 114 | 5-cyano-N-((1S,2S)-2-hydroxycyclohexyl)-6-methyl-4-(4-(1-methyl-1H-pyrazol-3-yl)benzyl)pyridine-2-carboxamide | | | 430.2 |
| 115 | 1,5-anhydro-2-(((5-cyano-6-methyl-4-(4-(1-methyl-1H-pyrazol-3-yl)benzyl)pyridin-2-yl)carbonyl)amino)-2,4-dideoxy-L-threo-pentitol | | | 432.1 |
| 116 | 4-((6-chloropyridin-3-yl)methyl)-N-((1S,2S)-2-hydroxycyclopentyl)-5,6-dimethylpyridine-2-carboxamide | | | 360.1 |

TABLE 1-15-continued

| Ex. No. | IUPAC name | structural formula | salt | MS |
|---|---|---|---|---|
| 117 | N-((1S,2S)-2-hydroxycyclopentyl)-5,6-dimethyl-4-((6-(1-methyl-1H-pyrazol-3-yl)pyridin-3-yl)methyl)pyridine-2-carboxamide | | | 406.2 |

Formulation Example 1

| (1) | compound obtained in Example 1 | 10.0 g |
|---|---|---|
| (2) | Lactose | 60.0 g |
| (3) | Cornstarch | 35.0 g |
| (4) | Gelatin | 3.0 g |
| (5) | Magnesium stearate | 2.0 g |

A mixture of the compound (10.0 g) obtained in Example 1, lactose (60.0 g) and cornstarch (35.0 g) is passed through a 1 mm mesh sieve and granulated by using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of sucrose, titanium dioxide, talc and gum arabic. The coated tablets are glazed with beeswax to give 1000 coated tablets.

Formulation Example 2

| (1) | compound obtained in Example 1 | 10.0 g |
|---|---|---|
| (2) | Lactose | 70.0 g |
| (3) | Cornstarch | 50.0 g |
| (4) | Soluble starch | 7.0 g |
| (5) | Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Measurement of M1 Receptor Positive Allosteric Modulator (M1PAM) Activity

The activity of a test compound in the presence of acetylcholine at EC20 concentration (final concentration 0.6-0.8 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A containing calcium indicator (Recording medium (DOJINDO LABORATORIES), 0.1% BSA (Wako Pure Chemical Industries, Ltd.), 2.5 µg/mL Fluo-4 AM (DOJINDO LABORATORIES), 0.08% Pluronic F127 (DOJINDO LABORATORIES), 1.25 mM probenecid (DOJINDO LABORATORIES)) was added at 30 µL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 2.4-3.2 nM acetylcholine was added at 10 µL/well, and the fluorescence was measured by FLIPRtetra (Molecular Devices) for 1 min every for 1 second. With the definition that the amount of change in the fluorescence on addition of acetylcholine (final concentration 1 µM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Example No. | activity (%) at 10 µM |
|---|---|
| 1 | 86 |
| 2 | 100 |
| 4 | 98 |
| 5 | 91 |
| 6 | 108 |
| 7 | 104 |
| 8 | 92 |
| 9 | 91 |
| 10 | 89 |
| 11 | 98 |
| 12 | 113 |
| 13 | 92 |
| 14 | 100 |
| 15 | 107 |
| 16 | 91 |
| 17 | 98 |
| 18 | 105 |
| 19 | 104 |
| 20 | 75 |
| 21 | 89 |

TABLE 2-continued

| Example No. | activity (%) at 10 μM |
|---|---|
| 22 | 77 |
| 23 | 84 |
| 24 | 87 |
| 25 | 85 |
| 26 | 59 |
| 27 | 88 |
| 28 | 73 |
| 29 | 93 |
| 30 | 85 |
| 31 | 84 |
| 32 | 101 |
| 33 | 71 |
| 34 | 96 |
| 35 | 102 |
| 36 | 95 |
| 37 | 106 |
| 38 | 101 |
| 39 | 100 |
| 40 | 95 |
| 41 | 95 |
| 42 | 106 |
| 43 | 92 |
| 44 | 92 |
| 45 | 102 |
| 46 | 101 |
| 47 | 96 |
| 48 | 106 |
| 49 | 99 |
| 50 | 105 |
| 51 | 95 |
| 52 | 100 |
| 53 | 93 |
| 54 | 99 |
| 55 | 97 |
| 56 | 103 |
| 57 | 95 |
| 58 | 89 |
| 59 | 90 |
| 60 | 87 |
| 61 | 108 |
| 62 | 96 |
| 63 | 94 |
| 64 | 104 |
| 65 | 106 |
| 66 | 105 |
| 67 | 95 |
| 68 | 96 |
| 69 | 100 |
| 70 | 87 |
| 71 | 69 |
| 72 | 105 |
| 73 | 94 |
| 74 | 103 |
| 75 | 102 |
| 76 | 92 |
| 77 | 100 |
| 78 | 104 |
| 79 | 106 |
| 80 | 84 |
| 81 | 97 |
| 82 | 103 |
| 83 | 103 |
| 84 | 93 |
| 85 | 99 |
| 86 | 95 |
| 87 | 92 |
| 88 | 99 |
| 89 | 101 |
| 90 | 106 |
| 91 | 98 |
| 92 | 99 |
| 93 | 105 |
| 94 | 101 |
| 95 | 99 |
| 96 | 112 |
| 97 | 93 |
| 98 | 94 |
| 99 | 96 |
| 100 | 97 |
| 101 | 105 |
| 102 | 104 |
| 103 | 109 |
| 104 | 102 |
| 105 | 100 |
| 106 | 104 |
| 107 | 101 |
| 108 | 114 |
| 109 | 95 |
| 110 | 95 |
| 111 | 90 |
| 112 | 91 |
| 113 | 94 |
| 114 | 94 |
| 115 | 111 |
| 116 | 104 |
| 117 | 106 |

Experimental Example 2

Measurement of Myo-Inositol 1 Phosphate (IP1)

Animals used were male Long-Evans rats. They were used after acclimation for at least 1 week. Test compounds were suspended in 0.5% (w/v) aqueous methylcellulose solution, and the suspension was orally administered to the rats. After a given time, lithium chloride was dissolved in saline and subcutaneously administered into the rats. After a given time, their bilateral hippocampi were isolated from the rats, and the wet weight thereof was measured. The isolated hippocampi were homogenized with HEPES buffer, followed by centrifugation. The IP1 and protein concentrations in the supernatant were measured by IP-One HTRF(R) assay kit (Cisbio Bioassays) and BCA protein assay kit (Thermo Scientific), respectively. The level of the IP1 production was expressed as the ratio of the concentration of IP1 to that of protein. The increase rate of the IP1 production was shown as a relative value when Vehicle administration group as 100%. The results are shown in Table 3.

TABLE 3

| test compound (mg/kg) | increase rate (%) |
|---|---|
| Example No. 1 (10 mg/kg) | 38 |
| Example No. 72 (10 mg/kg) | 70 |
| Example No. 74 (3 mg/kg) | 22 |

Experimental Example 3

Novel Object Recognition Test

Novel object recognition test is comprised of two trials called the acquisition and the retention trials. Scopolamine-induced memory deficits models were used for the test, and animals used were male Long-Evans rats (7-week-old). On the day before the test, for acclimation, the rats were allowed to freely move about the test box (40×40×50 cm) for 10 minutes. On the test day, the rats were acclimated to the test room for about for 1 hr prior to the test. The test compounds were orally administered to the rats in a single dose 2 hours before the acquisition trial. For induction of learning and memory deficits, scopolamine (0.1 mg/kg) was subcutaneously administered into the rats for 30 min before the acquisition trial. For the acquisition trial, two identical objects (A1, A2) were placed in the test box. The rats were put in the test box for 3 min, and the duration exploring each object was measured. The retention trial was performed for 4 hr after the acquisition trial. For the retention trial, one familiar object (A3) used for the acquisition trial and one novel object (B) having a different shape from A3 were placed in the test box. After setting the objects, the rats were introduced into the test box and retention trial was performed for 3 min. The duration for exploring each object in the acquisition trial and the retention trial was measured, and the exploration rate of novel object was calculated. The exploration rate of novel object was expressed as (the duration exploring the novel object)/[(the duration exploring the novel object)+(the duration exploring the familiar object)]×100(%) at mean±standard error. The results are shown below.

exploration rate of novel object (%)
control group: 69.26±2.87%
solvent-scopolamine group: 55.27±3.48%
Example No. 1 (10 mg/kg)-scopolamine group: 64.59±2.59%
control group: 66.74±3.01%
solvent-scopolamine group: 47.48±3.66%
Example No. 72 (3 mg/kg)-scopolamine group: 53.16±2.80%
Example No. 74 (10 mg/kg)-scopolamine group: 55.14±1.48%

INDUSTRIAL APPLICABILITY

The compound of the present invention may be useful as a cholinergic muscarinic M1 receptor positive allosteric modulator, or a medicament such as an agent for the prophylaxis or treatment of Alzheimer's disease, schizophrenia, pain, sleep disorder, Parkinson's disease dementia, dementia with Lewy bodies and the like, and the like.

This application is based on patent application No. 2014-122919 filed in Japan, the contents of which are encompassed in full herein.

The invention claimed is:

1. A compound represented by the formula (I):

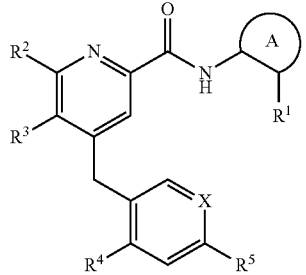

wherein
A is
a $C_{3-10}$ cycloalkyl group
which is optionally further substituted by 1 to 3 substituents selected from
(1) a halogen atom,
(2) a $C_{1-6}$ alkyl group optionally substituted by 1 to 3 hydroxy groups, and
(3) a $C_{1-6}$ alkoxy group;
$R^1$ is a hydrogen atom or a hydroxyl group;
$R^2$ is a hydrogen atom, a $C_{1-6}$ alkyl group or a $C_{1-6}$ alkoxy group;
$R^3$ is a hydrogen atom, a halogen atom, a cyano group, a $C_{1-6}$ alkyl group optionally substituted by 1 to 3 halogen atoms, a $C_{2-6}$ alkenyl group, a $C_{3-6}$ cycloalkyl group, or a $C_{1-6}$ alkoxy group optionally substituted by 1 to 3 halogen atoms;
$R^4$ is a hydrogen atom or a halogen atom;
$R^5$ is a pyrazolyl group optionally substituted by 1 to 3 $C_{1-6}$ alkyl groups; and
X is CH,
or a salt thereof.

2. The compound according to claim 1, wherein A is a $C_{3-10}$ cycloalkyl group;
$R^1$ is a hydroxyl group;
$R^2$ is a hydrogen atom or a $C_{1-6}$ alkyl group;
$R^3$ is a halogen atom, a cyano group, a $C_{1-6}$ alkyl group, or a $C_{1-6}$ alkoxy group;
$R^4$ is a hydrogen atom;
$R^5$ is a pyrazolyl group optionally substituted by 1 to 3 $C_{1-6}$ alkyl groups; and
X is CH,
or a salt thereof.

3. The compound according to claim 1, wherein A is a $C_{3-10}$ cycloalkyl group;
$R^1$ is a hydroxyl group;
$R^2$ is a hydrogen atom or a $C_{1-6}$ alkyl group;
$R^3$ is a $C_{1-6}$ alkyl group;
$R^4$ is a hydrogen atom;
$R^5$ is a pyrazolyl group optionally substituted by 1 to 3 $C_{1-6}$ alkyl groups; and
X is CH,
or a salt thereof.

4. N-((1S,2S)-2-hydroxycyclopentyl)-5-methyl-4-(4-(1-methyl-1H-pyrazol-3-yl)benzyl)pyridine-2-carboxamide or a salt thereof.

5. N-((1S,2S)-2-hydroxycyclopentyl)-5,6-dimethyl-4-(4-(1-methyl-1H-pyrazol-3-yl)benzyl)pyridine-2-carboxamide or a salt thereof.

6. A pharmaceutical composition comprising the compound according to claim 1 or a salt thereof, and a pharmaceutically acceptable carrier.

* * * * *